United States Patent
Lenser et al.

(10) Patent No.: US 9,526,662 B2
(45) Date of Patent: Dec. 27, 2016

(54) APPARATUSES AND METHODS FOR FOLDING ABSORBENT ARTICLES

(75) Inventors: Todd Douglas Lenser, Liberty Township, OH (US); Mark David Whaley, Liberty Township, OH (US)

(73) Assignee: The Procter & Gamble Company, Cincinnati, OH (US)

(*) Notice: Subject to any disclaimer, the term of this patent is extended or adjusted under 35 U.S.C. 154(b) by 864 days.

(21) Appl. No.: 13/368,378

(22) Filed: Feb. 8, 2012

(65) Prior Publication Data

US 2013/0203580 A1 Aug. 8, 2013

(51) Int. Cl.
B31F 1/10 (2006.01)
A61F 13/49 (2006.01)
A61F 13/15 (2006.01)

(52) U.S. Cl.
CPC ... *A61F 13/49061* (2013.01); *A61F 13/15747* (2013.01); *A61F 13/15772* (2013.01)

(58) Field of Classification Search
CPC .............. B65H 45/09; A61F 13/15747; A61F 2013/15796; A61F 13/15772; A61F 13/49061; A61F 13/15764
USPC ......................................................... 493/442
See application file for complete search history.

(56) References Cited

U.S. PATENT DOCUMENTS

| | | |
|---|---|---|
| 3,860,003 A | 1/1975 | Buell |
| 4,610,678 A | 9/1986 | Weisman et al. |
| 4,673,402 A | 6/1987 | Weisman et al. |
| 4,695,278 A | 9/1987 | Lawson |
| 4,704,115 A | 11/1987 | Buell |
| 4,795,454 A | 1/1989 | Dragoo |
| 4,834,735 A | 5/1989 | Alemany et al. |
| 4,888,231 A | 12/1989 | Angstadt |
| 4,909,803 A | 3/1990 | Aziz et al. |
| 5,562,646 A | 10/1996 | Goldman et al. |
| 5,599,335 A | 2/1997 | Goldman et al. |
| 5,628,097 A | 5/1997 | Benson et al. |
| 5,669,894 A | 9/1997 | Goldman et al. |
| 5,916,661 A | 6/1999 | Benson et al. |

(Continued)

FOREIGN PATENT DOCUMENTS

| | | |
|---|---|---|
| EP | 1 607 357 A1 | 12/2005 |
| EP | 1 504 738 B1 | 11/2007 |

(Continued)

OTHER PUBLICATIONS

WO International Search Report dated Apr. 12, 2013, 11 pages.

*Primary Examiner* — Robert Long
*Assistant Examiner* — Xavier A Madison
(74) *Attorney, Agent, or Firm* — Charles R. Matson

(57) ABSTRACT

The present disclosure relates to folding methods and apparatuses that operate to fold an advancing substrate in the cross direction along a central region to bring a second end region into a facing relationship with a first end region. In some embodiments, the second end region of the advancing substrate is folded around a folding axis 180° to bring the second end region into a facing relationship with the first end region. The folding axis may also be defined by an arc extending in the machine direction MD, wherein the second end region of the advancing substrate is helically folded toward the inside of the arc. A folding apparatus including a curved or arc-shaped folding axis may also be configured such the first and second web paths have substantially equal lengths.

4 Claims, 14 Drawing Sheets

(56) References Cited

U.S. PATENT DOCUMENTS

| | | | |
|---|---|---|---|
| 6,107,539 | A | 8/2000 | Palumbo et al. |
| 6,248,195 | B1 | 6/2001 | Schmitz |
| 6,545,197 | B1 | 4/2003 | Muller et al. |
| 6,546,987 | B1 | 4/2003 | Tachibana et al. |
| 6,790,798 | B1 | 9/2004 | Suzuki et al. |
| 6,913,664 | B2 | 7/2005 | Umebayashi et al. |
| 6,926,654 | B2 * | 8/2005 | Yamamoto et al. .......... 493/254 |
| 7,144,357 | B2 | 12/2006 | Yamamoto et al. |
| 7,383,865 | B2 | 6/2008 | Umebayashi et al. |
| 7,569,039 | B2 | 8/2009 | Matsuda et al. |
| 7,587,966 | B2 | 9/2009 | Nakakado et al. |
| 7,632,366 | B2 | 12/2009 | Shimizu et al. |
| 8,273,003 | B2 | 9/2012 | Umebayashi et al. |
| 2002/0174930 | A1 * | 11/2002 | Umebayashi et al. ....... 156/62.6 |
| 2004/0097895 | A1 | 5/2004 | Busam et al. |
| 2004/0158212 | A1 | 8/2004 | Ponomarenko et al. |
| 2005/0107764 | A1 | 5/2005 | Matsuda et al. |
| 2009/0312730 | A1 | 12/2009 | LaVon et al. |
| 2010/0179042 | A1 | 7/2010 | Yamamoto |
| 2010/0262110 | A1 | 10/2010 | Lakso |
| 2012/0021186 | A1 | 1/2012 | Schneider |
| 2012/0061015 | A1 | 3/2012 | LaVon et al. |
| 2012/0061016 | A1 | 3/2012 | LaVon et al. |
| 2013/0059714 | A1 | 3/2013 | Yamamoto et al. |

FOREIGN PATENT DOCUMENTS

| | | |
|---|---|---|
| EP | 2 380 540 A1 | 10/2011 |
| EP | 2 460 498 B1 | 7/2014 |
| WO | WO 2010/101284 A1 | 9/2010 |

* cited by examiner

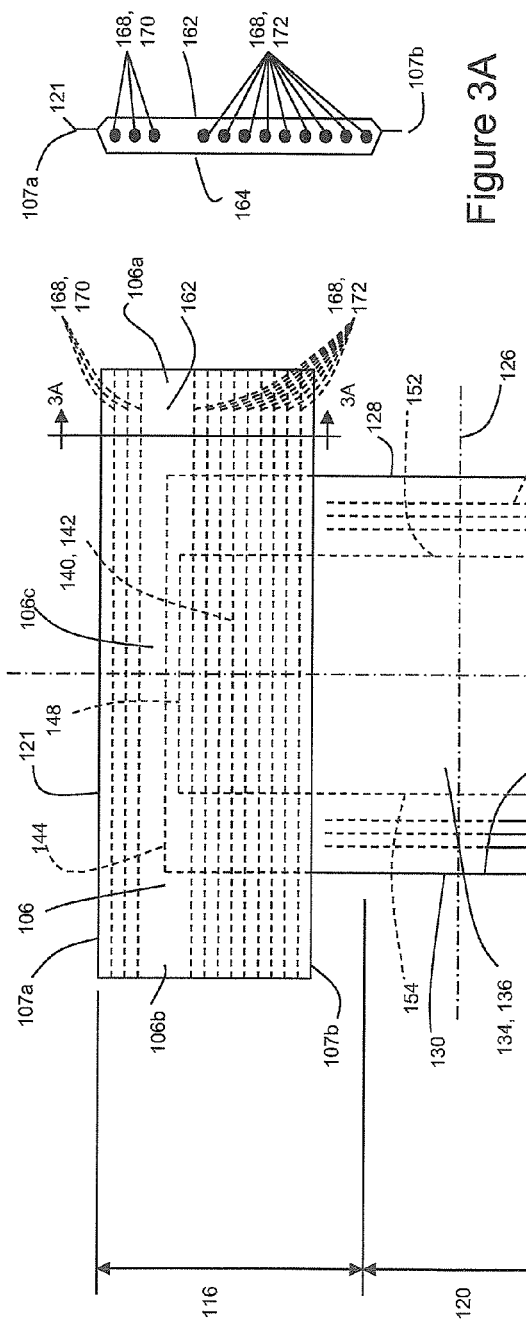

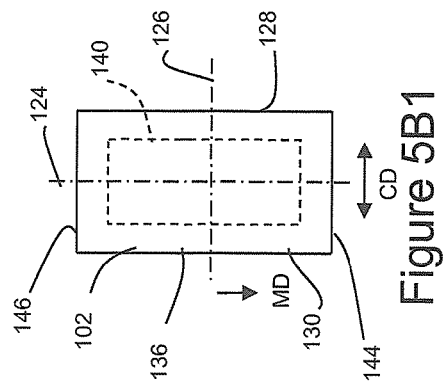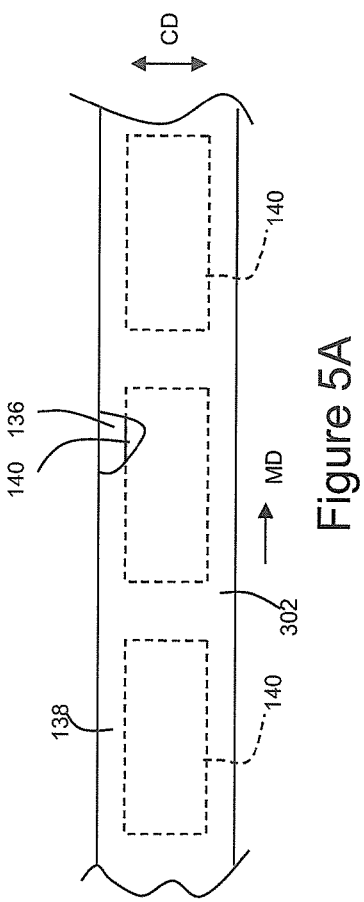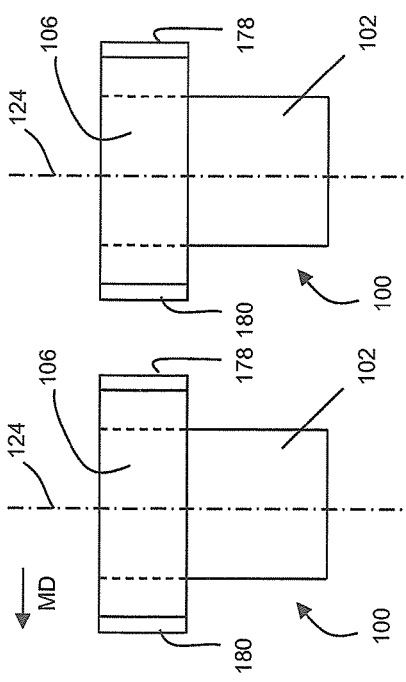

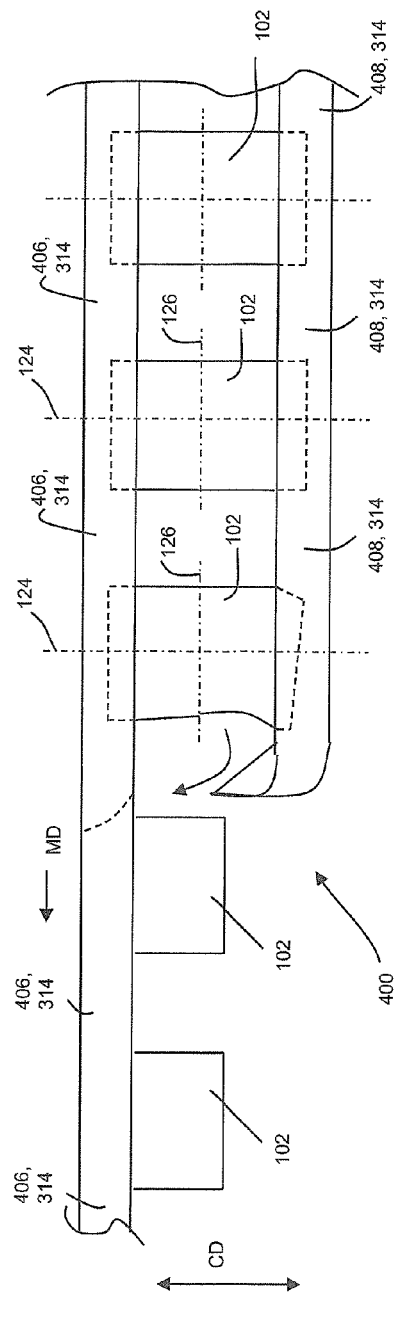
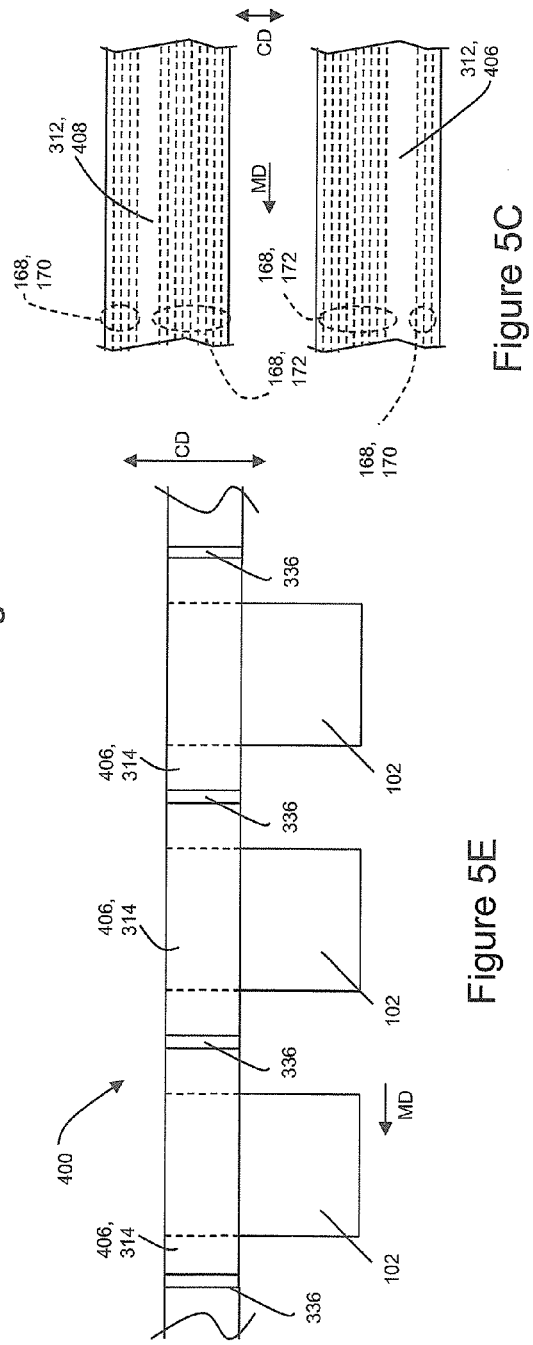
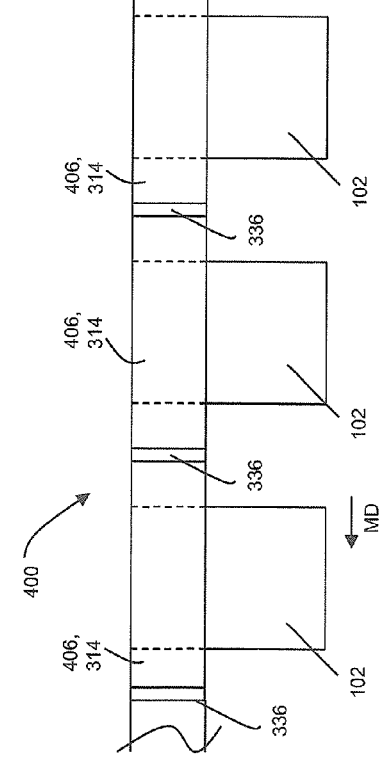
Figure 5D
Figure 5C
Figure 5E

APPARATUSES AND METHODS FOR FOLDING ABSORBENT ARTICLES

FIELD OF THE INVENTION

The present disclosure relates to methods for manufacturing absorbent articles, and more particularly, to apparatuses and methods for folding a continuous length of absorbent articles.

BACKGROUND OF THE INVENTION

Along an assembly line, various types of articles, such as for example, diapers and other absorbent articles, may be assembled by adding components to and/or otherwise modifying an advancing, continuous web of material. For example, in some processes, advancing webs of material are combined with other advancing webs of material. In other examples, individual components created from advancing webs of material are combined with advancing webs of material, which in turn, are then combined with other advancing webs of material. In some cases, individual components created from advancing web or webs are combined with other individual components created from other advancing web or webs. Webs of material and component parts used to manufacture diapers may include: backsheets, topsheets, leg cuffs, waist bands, absorbent core components, front and/or back ears, fastening components, and various types of elastic webs and components such as leg elastics, barrier leg cuff elastics, stretch side panels, and waist elastics. Once the desired component parts are assembled, the advancing web(s) and component parts are subjected to a final knife cut to separate the web(s) into discrete diapers or other absorbent articles.

In some converting configurations, discrete chassis spaced apart from each other are advanced in a machine direction and are arranged with a longitudinal axis parallel with the cross direction. Opposing waist regions of discrete chasses are then connected with continuous lengths of elastically extendable front and back belt webs advancing in the machine direction. While connected with the chassis, the front and back belt webs are maintained in a fully stretched condition along the machine direction, forming a continuous length of absorbent articles. The continuous length of absorbent articles may then be folded in a cross direction. During the folding process in some converting configurations, one of the front and back belt webs is folded 180° into a facing relationship with the opposing belt. However, the web path length of one of the belt webs may be longer than the opposing belt web. Such differing web path lengths may create problems associated with bringing the belt webs together in a desired alignment.

Consequently, it would be beneficial to provide a method and apparatus for folding a continuous length of absorbent articles that provides a reduction in mismatched web travel paths during the production process.

SUMMARY OF THE INVENTION

The present disclosure relates to folding methods and apparatuses that operate to fold an advancing substrate in the cross direction along a central region to bring a second end region into a facing relationship with a first end region. In some embodiments, the second end region of the advancing substrate is folded around a folding axis 180° to bring the second end region into a facing relationship with the first end region. The folding axis may also be defined by an arc extending in the machine direction MD, wherein the second end region of the advancing substrate is helically folded toward the inside of the arc. A folding apparatus including a curved or arc-shaped folding axis may also be configured such the first and second web paths have substantially equal lengths.

In one form, an apparatus may be configured for folding a continuous length of absorbent articles comprising a plurality of intermittently spaced chassis advancing in a machine direction, each chassis having a first end portion and an opposing second end portion separated from each other in the cross direction by a central portion, and each chassis having a first surface and an opposing second surface. The apparatus includes: a conveyor adapted to advance the first end portions of the chassis in the machine direction; a plurality of rollers adapted to advance the second end portions of the chassis in the machine direction, the plurality of rollers defining a web path that positions the second surface of the second end portion of the chassis into a facing relationship with second surface of the first end portion of the chassis as the chassis advance in machine direction; wherein the plurality of rollers are intermittently spaced along the machine direction, each roller having a rotation axis, the rotation axis of each roller being substantially perpendicular to a folding axis extending in the machine direction, wherein the central portions of the chassis are folded about the folding axis, and wherein the folding axis is curved.

In another form, a method may be configured for folding a continuous length of absorbent articles comprising a plurality of intermittently spaced chassis advancing in a machine direction, each chassis having a first end portion and an opposing second end portion separated from each other in the cross direction by a central portion, and each chassis having a first surface and an opposing second surface. The method includes the steps of: advancing the first end portions of the chassis in the machine direction; advancing the second end portions of the chassis in the machine direction along a web path that positions the second surface of the second end portion of the chassis into a facing relationship with second surface of the first end portion of the chassis as the chassis advance in machine direction; and folding the central portions of the chassis about a folding axis extending the machine direction, wherein the folding axis is curved.

BRIEF DESCRIPTION OF THE DRAWINGS

FIG. 2A is a partially cut away plan view of the diaper pant shown in FIG. 1.
FIG. 3A is a cross-sectional view of the diaper pants of FIGS. 2A and 2B taken along line 3A-3A.
FIG. 3B is a cross-sectional view of the diaper pants of FIGS. 2A and 2B taken along line 3B-3B.
FIG. 5A is a view of a continuous length of chassis assemblies from FIG. 4 taken along line A-A.
FIG. 5B1 is a view of a discrete chassis from FIG. 4 taken along line B1-B1.
FIG. 5B2 is a view of a discrete chassis from FIG. 4 taken along line B2-B2.

FIG. 5C is a view of continuous lengths of advancing front and back side panel material from FIG. 4 taken along line C-C.

FIG. 5D is a view of multiple discrete chassis spaced from each other along the machine direction MD and connected with each other by the front and back side panel material from FIG. 4 taken along line D-D.

FIG. 5E is a view of folded multiple discrete chassis with the front and back side panel material in a facing relationship from FIG. 4 taken along line E-E.

FIG. 5F is a view of two discrete absorbent articles advancing the machine direction MD from FIG. 4 taken along line F-F.

DETAILED DESCRIPTION OF THE INVENTION

Figure 1:
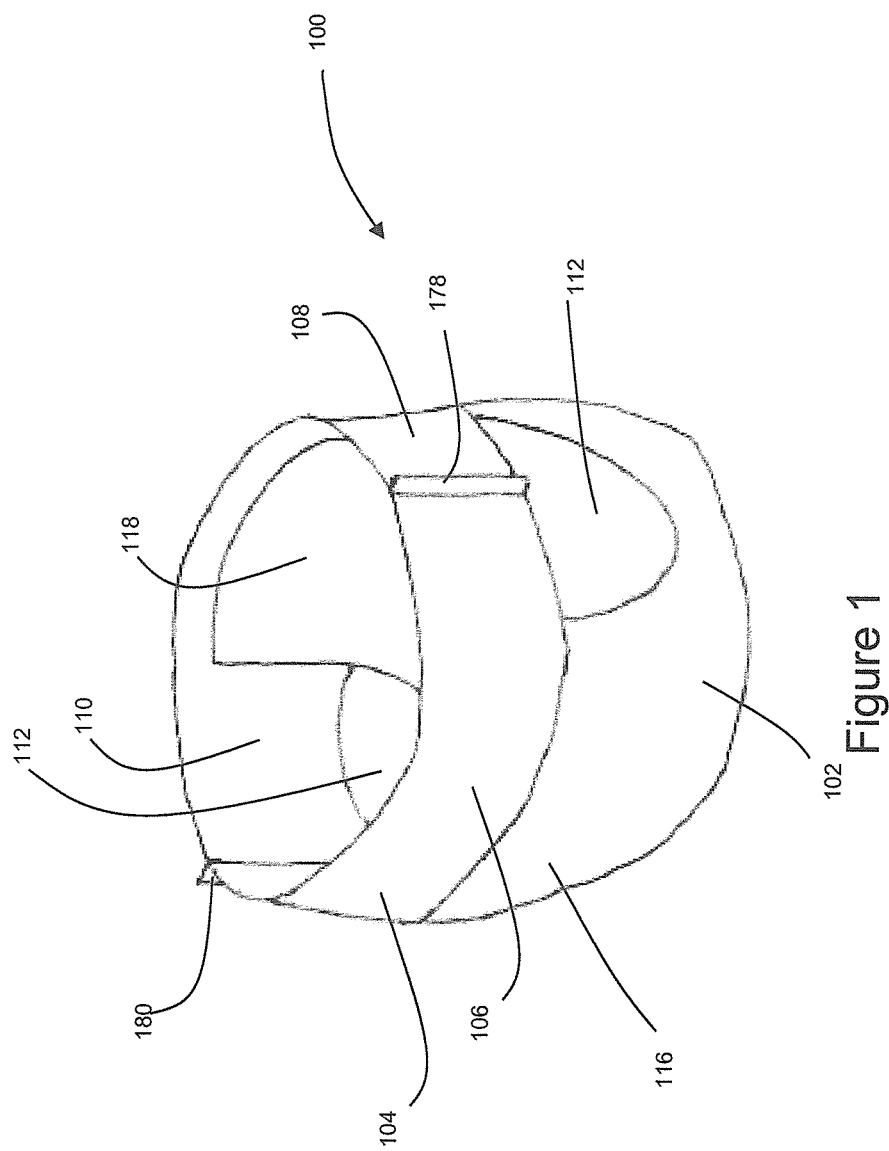
FIG. 1 is a perspective view of a diaper pant.

The following term explanations may be useful in understanding the present disclosure:

"Absorbent article" is used herein to refer to consumer products whose primary function is to absorb and retain soils and wastes. "Diaper" is used herein to refer to an absorbent article generally worn by infants and incontinent persons about the lower torso. The term "disposable" is used herein to describe absorbent articles which generally are not intended to be laundered or otherwise restored or reused as an absorbent article (e.g., they are intended to be discarded after a single use and may also be configured to be recycled, composted or otherwise disposed of in an environmentally compatible manner).

An "elastic," "elastomer" or "elastomeric" refers to materials exhibiting elastic properties, which include any material that upon application of a force to its relaxed, initial length can stretch or elongate to an elongated length more than 10% greater than its initial length and will substantially recover back to about its initial length upon release of the applied force.

As used herein, the term "joined" encompasses configurations whereby an element is directly secured to another element by affixing the element directly to the other element, and configurations whereby an element is indirectly secured to another element by affixing the element to intermediate member(s) which in turn are affixed to the other element.

"Longitudinal" means a direction running substantially perpendicular from a waist edge to a longitudinally opposing waist edge of an absorbent article when the article is in a flat out, uncontracted state, or from a waist edge to the bottom of the crotch, i.e. the fold line, in a bi-folded article. Directions within 45 degrees of the longitudinal direction are considered to be "longitudinal." "Lateral" refers to a direction running from a longitudinally extending side edge to a laterally opposing longitudinally extending side edge of an article and generally at a right angle to the longitudinal direction. Directions within 45 degrees of the lateral direction are considered to be "lateral."

The term "substrate" is used herein to describe a material which is primarily two-dimensional (i.e. in an XY plane) and whose thickness (in a Z direction) is relatively small (i.e. 1/10 or less) in comparison to its length (in an X direction) and width (in a Y direction). Non-limiting examples of substrates include a web, layer or layers or fibrous materials, nonwovens, films and foils such as polymeric films or metallic foils. These materials may be used alone or may comprise two or more layers laminated together. As such, a web is a substrate.

The term "nonwoven" refers herein to a material made from continuous (long) filaments (fibers) and/or discontinuous (short) filaments (fibers) by processes such as spunbonding, meltblowing, carding, and the like. Nonwovens do not have a woven or knitted filament pattern.

The term "machine direction" (MD) is used herein to refer to the direction of material flow through a process. In addition, relative placement and movement of material can be described as flowing in the machine direction through a process from upstream in the process to downstream in the process.

The term "cross direction" (CD) is used herein to refer to a direction that is generally perpendicular to the machine direction.

The term "pant" (also referred to as "training pant", "pre-closed diaper", "diaper pant", "pant diaper", and "pull-on diaper") refers herein to disposable absorbent articles having a continuous perimeter waist opening and continuous perimeter leg openings designed for infant or adult wearers. A pant can be configured with a continuous or closed waist opening and at least one continuous, closed, leg opening prior to the article being applied to the wearer. A pant can be preformed by various techniques including, but not limited to, joining together portions of the article using any refastenable and/or permanent closure member (e.g., seams, heat bonds, pressure welds, adhesives, cohesive bonds, mechanical fasteners, etc.). A pant can be preformed anywhere along the circumference of the article in the waist region (e.g., side fastened or seamed, front waist fastened or seamed, rear waist fastened or seamed).

"Pre-fastened" refers herein to pant diapers manufactured and provided to consumers in a configuration wherein the front waist region and the back waist region are fastened or connected to each other as packaged, prior to being applied to the wearer. As such pant diapers may have a continuous perimeter waist opening and continuous perimeter leg openings designed for infant or adult wearers. As discussed in more detail below, a diaper pant can be preformed by various techniques including, but not limited to, joining together portions of the diaper using refastenable and/or permanent closure members (e.g., seams, heat bonds, pressure welds, adhesives, cohesive bonds, mechanical fasteners, etc.). In addition, pant diapers can be preformed anywhere along the circumference of the waist region (e.g., side fastened or connected, front waist fastened or connected, rear waist fastened or connected).

The present disclosure relates to methods and apparatuses for folding substrates advancing in a machine direction. The substrates may have a continuous length extending the machine direction MD and may have a first end region and a second end region separated from each other along a cross direction CD by a central region. The folding methods and apparatuses discussed herein operate to fold the advancing substrate in the cross direction along the central region to bring the second end region into a facing relationship with the first end region. The folding apparatuses may include a folding axis about which the central region of the advancing substrate is folded. In some embodiments, the second end region of the advancing substrate is folded around the folding axis 180° to bring the second end region into a facing relationship with the first end region. As such, the first end region of the advancing substrate travels in the machine direction along a first web path during the folding process while the second end region of the substrate travels in the machine direction along a second web path defining a helical shape. The folding axis may also be defined by an arc extending in the machine direction MD, wherein the second end region of the advancing substrate is helically folded toward the inside of the arc. As discussed in more detail below, a folding apparatus including a curved or arc-shaped folding axis may be configured such the first and second web paths have substantially equal lengths.

It is to be appreciated that the folding methods and apparatuses herein may be configured to fold various types of substrates, the methods and apparatuses herein are discussed below in the context of manufacturing absorbent articles. In particular, the methods and apparatuses are discussed in the context of folding advancing, continuous lengths of absorbent articles during production. As discussed below, an advancing continuous length of absorbent articles may include a plurality of chassis connected with a continuous first belt substrate and a continuous second belt substrate. The continuous first and second belt substrates may be separated from each other along a cross direction while advancing along a machine direction MD. Each chassis may extend in the cross direction and may include opposing first and second end regions separated by a central region, wherein the first end regions are connected with first belt substrate and the second end regions are connected with the second belt substrate. The chassis may also be spaced from each other along the machine direction MD. The folding apparatus operates to fold the chassis around the folding axis along the central regions and to bring the second belt substrate and second end region of the chassis into a facing relationship with the first belt substrate and first end region of the chassis. In some embodiments, the second belt substrate and second end region of the chassis is folded 180° around the folding axis to bring the second belt substrate and second end region of the chassis into a facing relationship with the first belt substrate and first end region of the chassis. As such, the first belt substrate and first end region of the chassis travel in the machine direction along the first web path during the folding process while the second belt substrate and the second end region of the chassis travel in the machine direction along the second web path defining a helical shape. Thus, the second belt substrate and the second end region of the chassis are helically folded toward the inside of the arc of a curved folding axis. Again, the first and second web paths may have substantially equal lengths.

As discussed in more detail below, embodiments of the folding apparatus may include a conveyor and a plurality of rollers. The conveyor may be configured to advance the first end region of the substrate (or the first belt substrate and first end region of the chassis), and the rollers may be configured to advance the second end region of the substrate (or the second belt substrate and second end region of the chassis). The conveyor may define a portion of the first web path and the plurality of rollers may define the second web path. Each roller may have different angular orientations relative to another to provide a substantially helical shape to the second path along the machine direction MD. In some embodiments, the rotation axis of a roller may be angularly offset relative to a preceding roller upstream in the machine direction MD. As the second belt substrate and second waist regions of the chassis advance along the second web path, the relative angular positions between the rollers cause the second belt material substrate and second waist regions of the chassis to twist while advancing in the machine direction MD, and at the same time, fold the chassis along the folding axis to place the second belt substrate into a facing relationship with the first belt substrate.

As previously mentioned, the processes and apparatuses discussed herein may be used to fold various types of substrate configurations, some of which may be used in the manufacture of different types of absorbent articles. To help provide additional context to the subsequent discussion of the process embodiments, the following provides a general description of absorbent articles in the form of diapers that include components that may be folded in accordance with the methods and apparatuses disclosed herein.

FIGS. 1 and 2A show an example of a diaper pant 100 that may be assembled and folded in accordance with the apparatuses and methods disclosed herein. In particular, FIG. 1 shows a perspective view of a diaper pant 100 in a pre-fastened configuration, and FIG. 2A shows a plan view of the diaper pant 100 with the portion of the diaper that faces away from a wearer oriented towards the viewer. The diaper pant 100 shown in FIGS. 1 and 2A includes a chassis 102 and a ring-like elastic belt 104. As discussed below in more detail, a first elastic belt 106 and a second elastic belt 108 are connected together to form the ring-like elastic belt 104.

With continued reference to FIG. 2A, the chassis 102 includes a first waist region 116, a second waist region 118, and a crotch region 120 disposed intermediate the first and second waist regions. The first waist region 116 may be configured as a front waist region, and the second waist region 118 may be configured as back waist region. In some embodiments, the length of each of the front waist region, back waist region, and crotch region may be ⅓ of the length of the absorbent article 100. The diaper 100 may also include a laterally extending front waist edge 121 in the front waist region 116 and a longitudinally opposing and laterally extending back waist edge 122 in the back waist region 118. To provide a frame of reference for the present discussion, the diaper 100 and chassis 102 of FIG. 2A is shown with a longitudinal axis 124 and a lateral axis 126. In some embodiments, the longitudinal axis 124 may extend through the front waist edge 121 and through the back waist edge 122. And the lateral axis 126 may extend through a first longitudinal or right side edge 128 and through a midpoint of a second longitudinal or left side edge 130 of the chassis 102.

As shown in FIGS. 1 and 2A, the diaper pant 100 may include an inner, body facing surface 132, and an outer, garment facing surface 134. The chassis 102 may include a backsheet 136 and a topsheet 138. The chassis 102 may also include an absorbent assembly 140 including an absorbent core 142 may be disposed between a portion of the topsheet 138 and the backsheet 136. As discussed in more detail below, the diaper 100 may also include other features, such as leg elastics and/or leg cuffs to enhance the fit around the legs of the wearer.

As shown in FIG. 2A, the periphery of the chassis 102 may be defined by the first longitudinal side edge 128, a second longitudinal side edge 130; a first laterally extending end edge 144 disposed in the first waist region 116; and a second laterally extending end edge 146 disposed in the second waist region 118. Both side edges 128 and 130 extend longitudinally between the first end edge 144 and the second end edge 146. As shown in FIG. 2A, the laterally extending end edges 144 and 146 are located longitudinally inward from the laterally extending front waist edge 121 in the front waist region 116 and the laterally extending back waist edge 122 in the back waist region 118. When the diaper pant 100 is worn on the lower torso of a wearer, the front waist edge 120 and the back waist edge 122 of the chassis 102 may encircle a portion of the waist of the wearer. At the same time, the chassis side edges 128 and 130 may encircle at least a portion of the legs of the wearer. And the crotch region 119 may be generally positioned between the legs of the wearer with the absorbent core 142 extending from the front waist region 116 through the crotch region 119 to the back waist region 118.

It is to also be appreciated that a portion or the whole of the diaper 100 may also be made laterally extensible. The additional extensibility may help allow the diaper 100 to conform to the body of a wearer during movement by the wearer. The additional extensibility may also help, for example, allow the user of the diaper 100 including a chassis 102 having a particular size before extension to extend the front waist region 116, the back waist region 118, or both waist regions of the diaper 100 and/or chassis 102 to provide additional body coverage for wearers of differing size, i.e., to tailor the diaper to an individual wearer. Such extension of the waist region or regions may give the absorbent article a generally hourglass shape, so long as the crotch region is extended to a relatively lesser degree than the waist region or regions, and may impart a tailored appearance to the article when it is worn.

As previously mentioned, the diaper pant 100 may include a backsheet 136. The backsheet 136 may also define the outer surface 134 of the chassis 102. The backsheet 136 may be impervious to fluids (e.g., menses, urine, and/or runny feces) and may be manufactured from a thin plastic film, although other flexible liquid impervious materials may also be used. The backsheet 136 may prevent the exudates absorbed and contained in the absorbent core from wetting articles which contact the diaper 100, such as bedsheets, pajamas and undergarments. The backsheet 136 may also comprise a woven or nonwoven material, polymeric films such as thermoplastic films of polyethylene or polypropylene, and/or a multi-layer or composite materials comprising a film and a nonwoven material (e.g., having an inner film layer and an outer nonwoven layer). The backsheet may also comprise an elastomeric film. An example backsheet 136 may be a polyethylene film having a thickness of from about 0.012 mm (0.5 mils) to about 0.051 mm (2.0 mils). Exemplary polyethylene films are manufactured by Clopay Corporation of Cincinnati, Ohio, under the designation BR-120 and BR-121 and by Tredegar Film Products of Terre Haute, Ind., under the designation XP-39385. The backsheet 136 may also be embossed and/or matte-finished to provide a more clothlike appearance. Further, the backsheet 136 may permit vapors to escape from the absorbent core (i.e., the backsheet is breathable) while still preventing exudates from passing through the backsheet 136. The size of the backsheet 136 may be dictated by the size of the absorbent core 142 and/or particular configuration or size of the diaper 100.

Also described above, the diaper pant 100 may include a topsheet 138. The topsheet 138 may also define all or part of the inner surface 132 of the chassis 102. The topsheet 138 may be compliant, soft feeling, and non-irritating to the wearer's skin. It may be elastically stretchable in one or two directions. Further, the topsheet 138 may be liquid pervious, permitting liquids (e.g., menses, urine, and/or runny feces) to penetrate through its thickness. A topsheet 138 may be manufactured from a wide range of materials such as woven and nonwoven materials; apertured or hydroformed thermoplastic films; apertured nonwovens, porous foams; reticulated foams; reticulated thermoplastic films; and thermoplastic scrims. Woven and nonwoven materials may comprise natural fibers such as wood or cotton fibers; synthetic fibers such as polyester, polypropylene, or polyethylene fibers; or combinations thereof. If the topsheet 138 includes fibers, the fibers may be spunbond, carded, wet-laid, meltblown, hydroentangled, or otherwise processed as is known in the art.

Topsheets 138 may be selected from high loft nonwoven topsheets, apertured film topsheets and apertured nonwoven topsheets. Apertured film topsheets may be pervious to bodily exudates, yet substantially non-absorbent, and have a reduced tendency to allow fluids to pass back through and rewet the wearer's skin. Exemplary apertured films may include those described in U.S. Pat. Nos. 5,628,097; 5,916,661; 6,545,197; and 6,107,539.

As mentioned above, the diaper pant 100 may also include an absorbent assembly 140 that is joined to the chassis 102. As shown in FIG. 2A, the absorbent assembly 140 may have a laterally extending front edge 148 in the front waist region 116 and may have a longitudinally opposing and laterally extending back edge 150 in the back waist region 118. The absorbent assembly may have a longitudinally extending right side edge 152 and may have a laterally opposing and longitudinally extending left side edge 154, both absorbent assembly side edges 152 and 154 may extend longitudinally between the front edge 148 and the back edge 150. The absorbent assembly 140 may additionally include one or more absorbent cores 142 or absorbent core layers. The absorbent core 142 may be at least partially disposed between the topsheet 138 and the backsheet 136 and may be formed in various sizes and shapes that are compatible with the diaper. Exemplary absorbent structures for use as the absorbent core of the present disclosure are described in U.S. Pat. Nos. 4,610,678; 4,673,402; 4,888,231; and 4,834,735.

Some absorbent core embodiments may comprise fluid storage cores that contain reduced amounts of cellulosic airfelt material. For instance, such cores may comprise less than about 40%, 30%, 20%, 10%, 5%, or even 1% of cellulosic airfelt material. Such a core may comprises primarily absorbent gelling material in amounts of at least about 60%, 70%, 80%, 85%, 90%, 95%, or even about 100%, where the remainder of the core comprises a microfiber glue (if applicable). Such cores, microfiber glues, and absorbent gelling materials are described in U.S. Pat. Nos. 5,599,335; 5,562,646; 5,669,894; and 6,790,798 as well as U.S. Patent Publication Nos. 2004/0158212 and 2004/0097895.

As previously mentioned, the diaper 100 may also include elasticized leg cuffs 156. It is to be appreciated that the leg cuffs 156 can be and are sometimes also referred to as leg bands, side flaps, barrier cuffs, elastic cuffs or gasketing cuffs. The elasticized leg cuffs 156 may be configured in various ways to help reduce the leakage of body exudates in the leg regions. Example leg cuffs 156 may include those described in U.S. Pat. Nos. 3,860,003; 4,909,803; 4,695,278; 4,795,454; 4,704,115; 4,909,803; and U.S. patent application Ser. No. 12/434,984.

As mentioned above, diaper pants may be manufactured with a ring-like elastic belt 104 and provided to consumers in a configuration wherein the front waist region 116 and the back waist region 118 are connected to each other as packaged, prior to being applied to the wearer. As such, diaper pants may have a continuous perimeter waist opening 110 and continuous perimeter leg openings 112 such as shown in FIG. 1.

As previously mentioned, the ring-like elastic belt 104 is defined by a first elastic belt 106 connected with a second elastic belt 108. As shown in FIG. 2A, the first elastic belt 106 defines first and second opposing end regions 106a, 106b and a central region 106c, and the second elastic 108 belt defines first and second opposing end regions 108a, 108b and a central region 108c.

The central region 106c of the first elastic belt is connected with the first waist region 116 of the chassis 102, and the central region 108c of the second elastic belt 108 is connected with the second waist region 118 of the chassis 102. As shown in FIG. 1, the first end region 106a of the first elastic belt 106 is connected with the first end region 108a of the second elastic belt 108 at first side seam 178, and the second end region 106b of the first elastic belt 106 is connected with the second end region 108b of the second elastic belt 108 at second side seam 180 to define the ring-like elastic belt 104 as well as the waist opening 110 and leg openings 112.

As shown in FIGS. 2A, 3A, and 3B, the first elastic belt 106 also defines an outer lateral edge 107a and an inner lateral edge 107b, and the second elastic belt 108 defines an outer lateral edge 109a and an inner lateral edge 109b. The outer lateral edges 107a, 107b may also define the front waist edge 120 and the laterally extending back waist edge 122. The first elastic belt and the second elastic belt may also each include an outer, garment facing layer 162 and an inner, wearer facing layer 164. It is to be appreciated that the first elastic belt 106 and the second elastic belt 108 may comprise the same materials and/or may have the same structure. In some embodiments, the first elastic belt 106 and the second elastic belt may comprise different materials and/or may have different structures. It should also be appreciated that the first elastic belt 106 and the second elastic belt 108 may be constructed from various materials. For example, the first and second belts may be manufactured from materials such as plastic films; apertured plastic films; woven or nonwoven webs of natural materials (e.g., wood or cotton fibers), synthetic fibers (e.g., polyolefins, polyamides, polyester, polyethylene, or polypropylene fibers) or a combination of natural and/or synthetic fibers; or coated woven or nonwoven webs. In some embodiments, the first and second elastic belts include a nonwoven web of synthetic fibers, and may include a stretchable nonwoven. In other embodiments, the first and second elastic belts include an inner hydrophobic, non-stretchable nonwoven material and an outer hydrophobic, non-stretchable nonwoven material.

The first and second elastic belts 106, 108 may also each include belt elastic material interposed between the outer layer 162 and the inner layer 164. The belt elastic material may include one or more elastic elements such as strands, ribbons, or panels extending along the lengths of the elastic belts. As shown in FIGS. 2A, 3A, and 3B, the belt elastic material may include a plurality of elastic strands 168 which may be referred to herein as outer, waist elastics 170 and inner, waist elastics 172. As shown in FIG. 2A, the elastic strands 168 continuously extend laterally between the first and second opposing end regions 106a, 106b of the first elastic belt 106 and between the first and second opposing end regions 108a, 108b of the second elastic belt 108. In some embodiments, some elastic strands 168 may be configured with discontinuities in areas, such as for example, where the first and second elastic belts 106, 108 overlap the absorbent assembly 140. In some embodiments, the elastic strands 168 may be disposed at a constant interval in the longitudinal direction. In other embodiments, the elastic strands 168 may be disposed at different intervals in the longitudinal direction. The belt elastic material in a stretched condition may be interposed and joined between the uncontracted outer layer and the uncontracted inner layer. When the belt elastic material is relaxed, the belt elastic material returns to an unstretched condition and contracts the outer layer and the inner layer. The belt elastic material may provide a desired variation of contraction force in the area of the ring-like elastic belt.

Figure 2B:
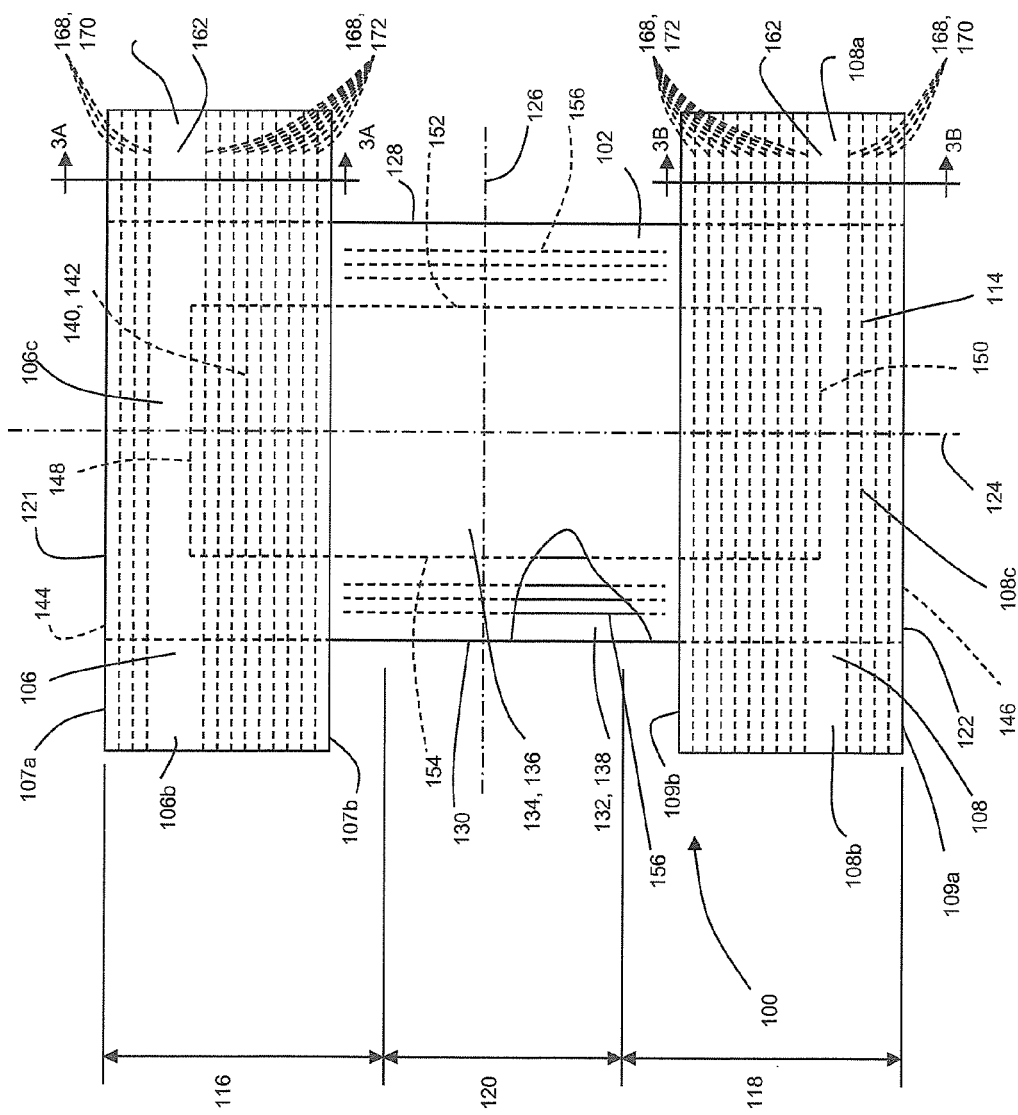
FIG. 2B is a partially cut away plan view of a second embodiment of a diaper pant.

It is to be appreciated that the chassis 102 and elastic belts 106, 108 may be configured in different ways other than as depicted in FIG. 2A. For example, FIG. 2B shows a plan view of a diaper pant 100 having the same components as described above with reference to FIG. 2A, except the first laterally extending end edge 144 of the chassis 102 is aligned along and coincides with the outer lateral edge 107a of the first elastic belt 106, and the second laterally extending end edge 146 is aligned along and coincides with the outer lateral edge 109a of the second belt 108.

Figure 4:
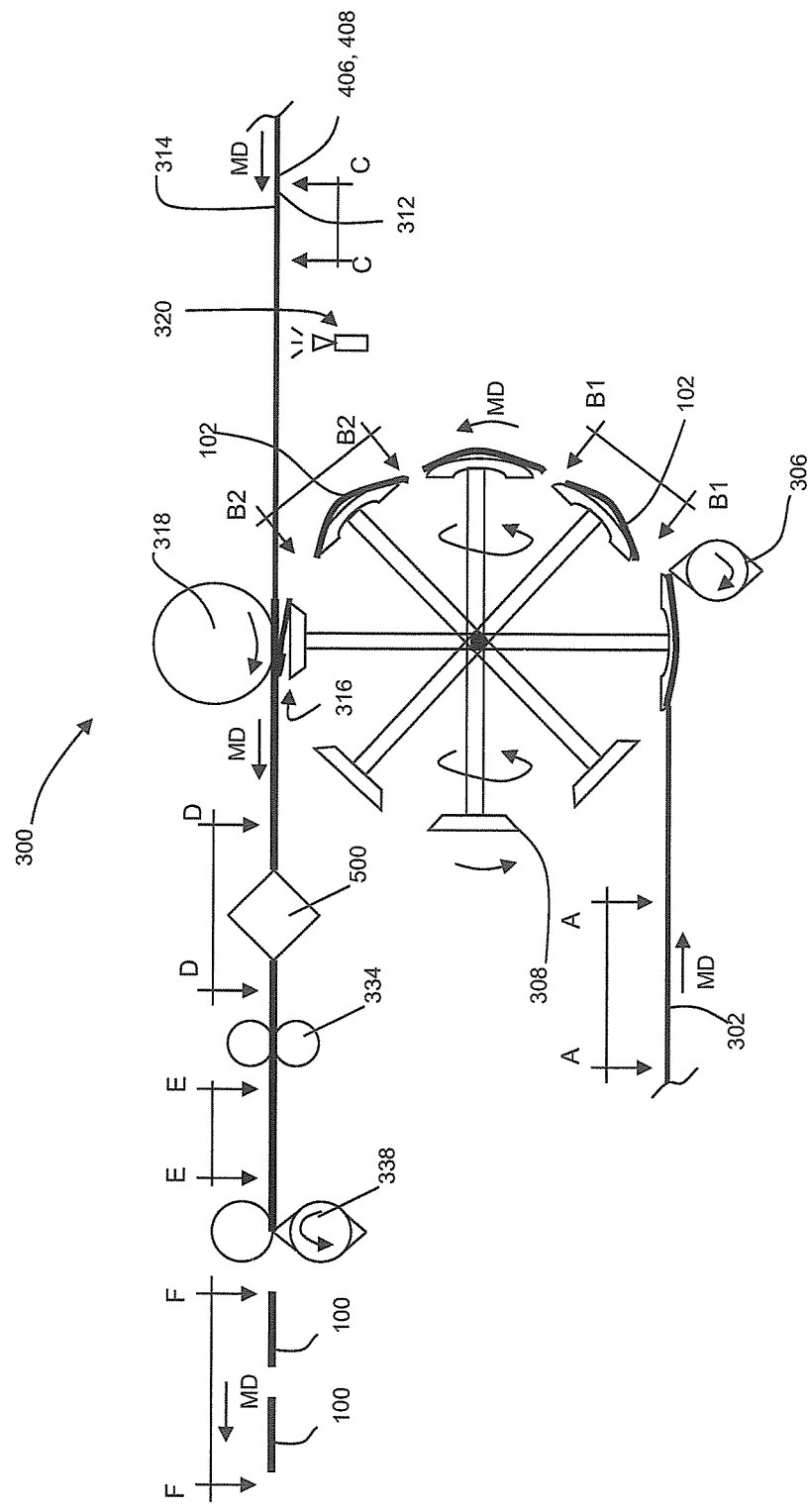
FIG. 4 is a schematic side view of a converting apparatus adapted to manufacture pre-fastened, pant diapers.

As previously mentioned, the apparatuses and methods according to the present disclosure may be utilized to assemble various components of pre-fastened, refastenable pant diapers 100. For example, FIG. 4 shows a schematic view of a converting apparatus 300 adapted to manufacture pant diapers 100. The method of operation of the converting apparatus 300 may described with reference to the various components of pant diapers 100 described above and shown in FIGS. 1 and 2A. Although the following methods are provided in the context of the diaper 100 shown in FIGS. 1 and 2A, it is to be appreciated that various embodiments of diaper pants can be manufactured according the methods disclosed herein, such as for example, the absorbent articles disclosed in U.S. Pat. No. 7,569,039, filed on Nov. 10, 2004; U.S. Patent Publication No. 2005/0107764A1, filed on Nov. 10, 2004; U.S. patent application Ser. No. 13/221,127, filed on Aug. 30, 2011; and U.S. patent application Ser. No. 13/221,104, filed on Aug. 30, 2011, which are all hereby incorporated by reference herein.

As described in more detail below, the converting apparatus 300 shown in FIG. 4 operates to advance discrete chassis 102 along a machine direction MD such that the lateral axis of each chassis 102 is parallel with the machine direction, and wherein the chassis 102 are spaced apart from each other along the machine direction. Opposing waist regions 116, 118 of the spaced apart chassis 102 are then connected with continuous lengths of advancing first and second elastic belt substrates 406, 408. The chassis 102 are then folded along the lateral axis to bring the first and second elastic belt substrates 406, 408 into a facing relationship, and the first and second elastic belt substrates are connected together along intermittently spaced seams 336. And the elastic belt substrates 406, 408 are cut along the seams 336 to create discrete diapers 100, such as shown in FIG. 1.

As shown in FIGS. 4 and 5A, a continuous length of chassis assemblies 302 are advanced in a machine direction MD to a carrier apparatus 308 and cut into discrete chassis 102 with knife roll 306. The continuous length of chassis assemblies may include absorbent assemblies 140 sandwiched between topsheet material 138 and backsheet material 136, leg elastics, barrier leg cuffs and the like. A portion of the chassis assembly is cut-away to show a portion of the topsheet material 138 and an absorbent assembly 140.

After the discrete absorbent chassis 102 are cut by the knife roll 306, the carrier apparatus 308 rotates and advances the discrete chassis 102 in the machine direction MD in the orientation shown in FIG. 5B1, wherein the longitudinal axis 124 of the chassis 102 is generally parallel with the machine direction MD. While the chassis 102 shown in FIG. 5B1 is shown with the first laterally extending end edge 144 as a leading edge and the second laterally extending end edge 146 as the trailing edge, it is to be appreciated that in other embodiments, the chassis 102 may be advanced in other orientations. For example, the chassis may be oriented such that the first laterally extending end edge 144 is a trailing edge and the second laterally extending end edge 146 is a leading edge. The carrier apparatus 308 also rotates while at the same time changing the orientation of the advancing chassis 102. The carrier apparatus 308 may also change the speed at which the chassis 102 advances in the machine direction MD. It is to be appreciated that various forms of carrier apparatuses may be used with the methods herein, such as for example, the carrier apparatuses disclosed in U.S. Pat. No. 7,587,966. FIG. 5B2 shows the orientation of the chassis 102 on the carrier apparatus 308 while advancing in the machine direction. More particularly, FIG. 5B2 shows the chassis 102 with the lateral axis 126 of the chassis 102 generally parallel with the machine direction MD, and wherein the first longitudinal side edge 128 is the leading edge and the second longitudinal side edge 130 is the trailing edge.

As discussed below with reference to FIGS. 3, 5C, 5D, 5E, and 5F, the chassis 102 are transferred from the carrier apparatus 308 and combined with advancing, continuous lengths of belt substrates 406, 408, which are subsequently cut to form first and second elastic belts 106, 108 on diapers 100.

With reference to FIGS. 3 and 5C, the chassis 102 are transferred from the carrier apparatus 308 to a nip 316 between the carrier apparatus 308 and a carrier apparatus 318 where the chassis 102 is combined with continuous lengths of advancing front belt 406 and back belt 408 substrate material. The front belt substrate material 406 and the back belt substrate material 408 each define a wearer facing surface 312 and an opposing garment facing surface 314. The wearer facing surface 312 of the first belt substrate 406 may be combined with the garment facing surface 134 of the chassis 102 along the first waist region 116, and the wearer facing surface 312 of the second belt substrate 408 may be combined with the garment facing surface 134 of the chassis 102 along the second waist region 118. As shown in FIG. 4, adhesive 320 may be intermittently applied to the wearer facing surface 312 of the first and second belt substrates 406, 408 before combining with the discrete chassis 102 at the nip 316 between roll 318 and the carrier apparatus 308.

With reference to FIGS. 4 and 5D, a continuous length of absorbent articles 400 are defined by multiple discrete chassis 102 spaced from each other along the machine direction MD and connected with each other by the second belt substrate 408 and the first belt substrate 406. As shown in FIG. 4, the continuous length of absorbent articles 400 advances from the nip 316 to a folding apparatus 500. At the folding apparatus 500, each chassis 102 is folded in the cross direction CD along a lateral axis 126 to place the first waist region 116, and specifically, the inner, body facing surface 132 into a facing, surface to surface orientation with the inner, body surface 132 of the second waist region 118. The folding of the chassis also positions the wearer facing surface 312 of the second belt substrate 408 extending between each chassis 102 in a facing relationship with the wearer facing surface 312 of the first belt substrate 406 extending between each chassis 102. As shown in FIGS. 4, 5D, and 5E, the folded discrete chassis 102 connected with the first and second belt substrates 406, 408 are advanced from the folding apparatus 500 to a bonder 334. The bonder 334 operates to bond a portion of the second belt substrate 408 extending between each chassis 102 with a portion of the first belt substrate 406 extending between each chassis 102, thus creating discrete bond regions 336. It is to be appreciated that various types of bonder apparatuses and methods can be used to bond the second belt substrate material 408 with the first belt substrate material 406, such as for example disclosed in U.S. Pat. Nos. 6,248,195; 6,546,987; and 7,383,865, as well as U.S. patent application Ser. No. 12/795,021, filed Jun. 7, 2010, which are incorporated by reference herein.

As shown in FIGS. 4 and 5F, a continuous length of absorbent articles are advanced from the bonder 334 to a knife roll 338 where the discrete bond regions 336 are cut into along the cross direction to create a first side seam 178 on an absorbent article 100 and a second side seam 180 on a subsequently advancing absorbent article.

Figure 6:
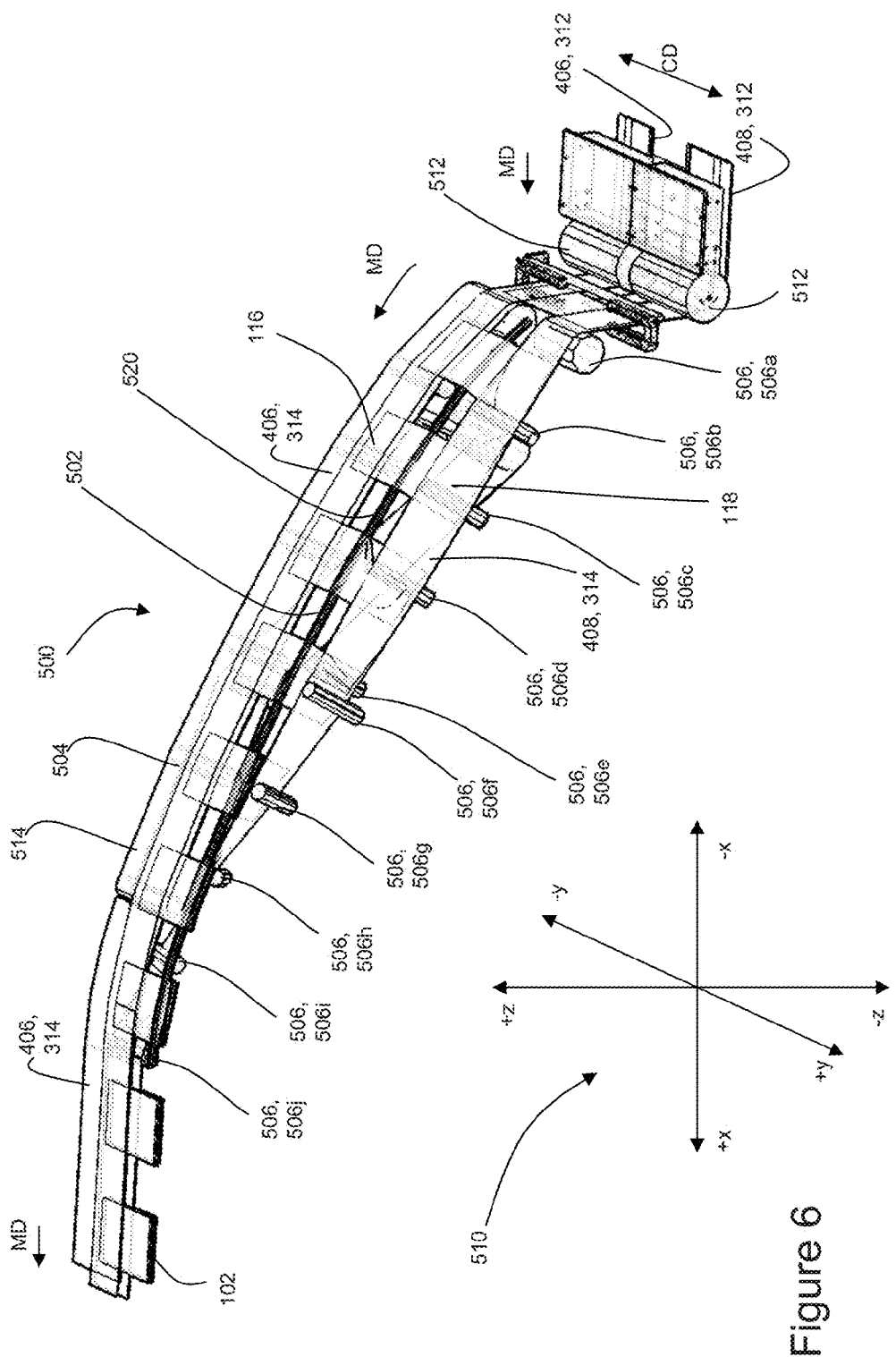
FIG. 6 is an isometric side view of a continuous length of absorbent articles advancing in a machine direction MD along an embodiment of a folding apparatus.
Figure 7:
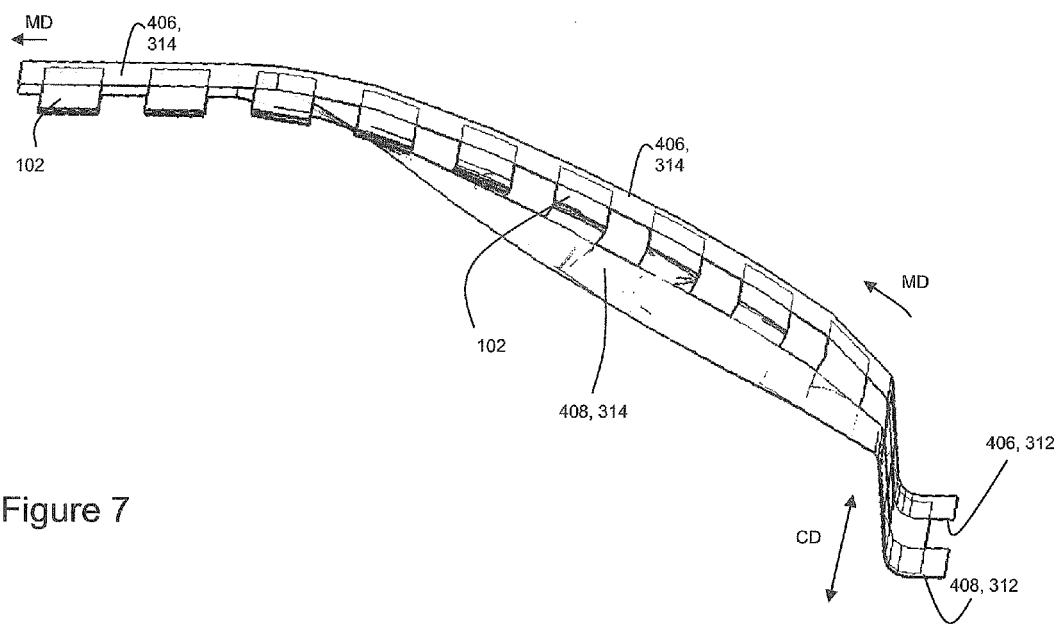
FIG. 7 is an isometric side view of the continuous length of absorbent articles of FIG. 6.

As previously mentioned with reference to FIG. 4, the converting apparatus may include a folding apparatus 500 to fold the chassis 102 of the continuous length of absorbent articles 400 in the cross direction CD. FIGS. 6 and 7 show an isometric view of a continuous length of absorbent articles 400 advancing in a machine direction MD along an embodiment of a folding apparatus 500. The folding apparatus 500 folds the chassis 102 along a folding axis 502 to position the wearer facing surface 312 of the second belt substrate 408 in a facing relationship with the wearer facing surface 312 of the first belt substrate 406. The folding apparatus also operates to fold each chassis 102 in the cross direction CD along the folding axis 502 to place the first waist region 116, and specifically, the inner, body facing surface 132 of the first waist region 116 into a facing, surface to surface orientation with the inner, body surface 132 of the second waist region 118.

As shown in FIGS. 6, 8, 9, and 10, the folding apparatus 500 may include a conveyor 504 and a plurality of rollers 506. In the converting arrangement shown in FIG. 6, the conveyor 504 is adapted to advance first end portions of the chassis 102, such as the first waist region 116, and the first belt material substrate 406 in the machine direction MD along a first web path. And the plurality of rollers 506 is adapted to advance second end portions of the chassis 102, such as the second waist region 118, and the second belt material substrate 408 in the machine direction MD along a second web path. As discussed in more detail below, each roller 506 may have different angular orientations relative to another to provide a substantially helical shape to the second path along the machine direction MD. It is to be appreciated that the folding apparatus may include various other arrangements of components than those described and shown in herein. For example, some embodiments of the folding apparatus may include a plurality of rollers instead of a conveyor 504, and may include a twisted belt conveyor arrangement instead of a plurality of rollers 506.

As previously mentioned, the folding apparatus 500 may include conveyor 504 and the plurality of rollers 506. For example, the conveyor 504 of the folding apparatus 500 shown in FIGS. 6, 8, 9, and 10 includes a belt 514 that advances the first belt material substrate 406 and first waist regions 116 of the chassis 102 along the first web path. The folding apparatus 500 also includes ten rollers 506, labeled as 506a through 506j, that advance the second belt material substrate 408 and second waist regions 118 of the chassis 102 along the second web path. Each roller 506 defines a rotation axis 508 (labeled 508a through 508j). As discussed in more detail below, the rotation axis of a roller 506 may be angularly offset relative to a preceding roller 506 upstream in the machine direction MD. As the second belt material substrate 408 and second waist regions 118 of the chassis 102 advance along the second web path, the relative angular positions between the rollers 506 cause the second belt material substrate 408 and second waist regions 118 of the chassis 102 to twist while advancing in the machine direction MD, and at the same time, fold the chassis 102 along the folding axis 502 to place the second belt substrate 408 into a facing relationship with the first belt substrate 406. The folding axis 502 may also be defined by an arc extending in the machine direction MD, wherein second belt material substrate 408 and second end region of the chassis are helically folded toward the inside of the arc. As discussed in more detail below, the curved or arc-shaped folding axis may be configured such the first and second web paths have substantially equal lengths.

With continued reference to FIG. 6, an x-y-z axis coordinate system 510 is provided to help provide additional reference to the description of the folding apparatus 500. As shown in FIG. 6, the first belt material substrate 406, second belt material substrate 408, and chassis 102 advance toward rollers 512 along the machine direction MD in the +x direction, with a cross direction CD along the ±y direction. After passing the rollers 512, the first belt material substrate 406, second belt material substrate 408, and chassis 102 advance toward the folding apparatus 500 along the machine direction MD in the +z direction, with a cross direction CD along the ±y direction. More particularly, the first belt material substrate 406 and first waist regions 116 of the chassis 102 advance from the roller 512 in the +z direction to the belt 514 of the folding apparatus 500, and the second belt material substrate 408 and second waist regions 118 of the chassis 102 advance from the roller 512 in the +z direction to the first roller 506a of the folding apparatus 500. As such, before engaging the folding apparatus 500, the first belt material substrate 406, second belt material substrate 408, and chassis 102 advance in the machine direction MD along a substantially two-dimensional plane (e.g. x-y plane or y-z plane).

Figure 8:
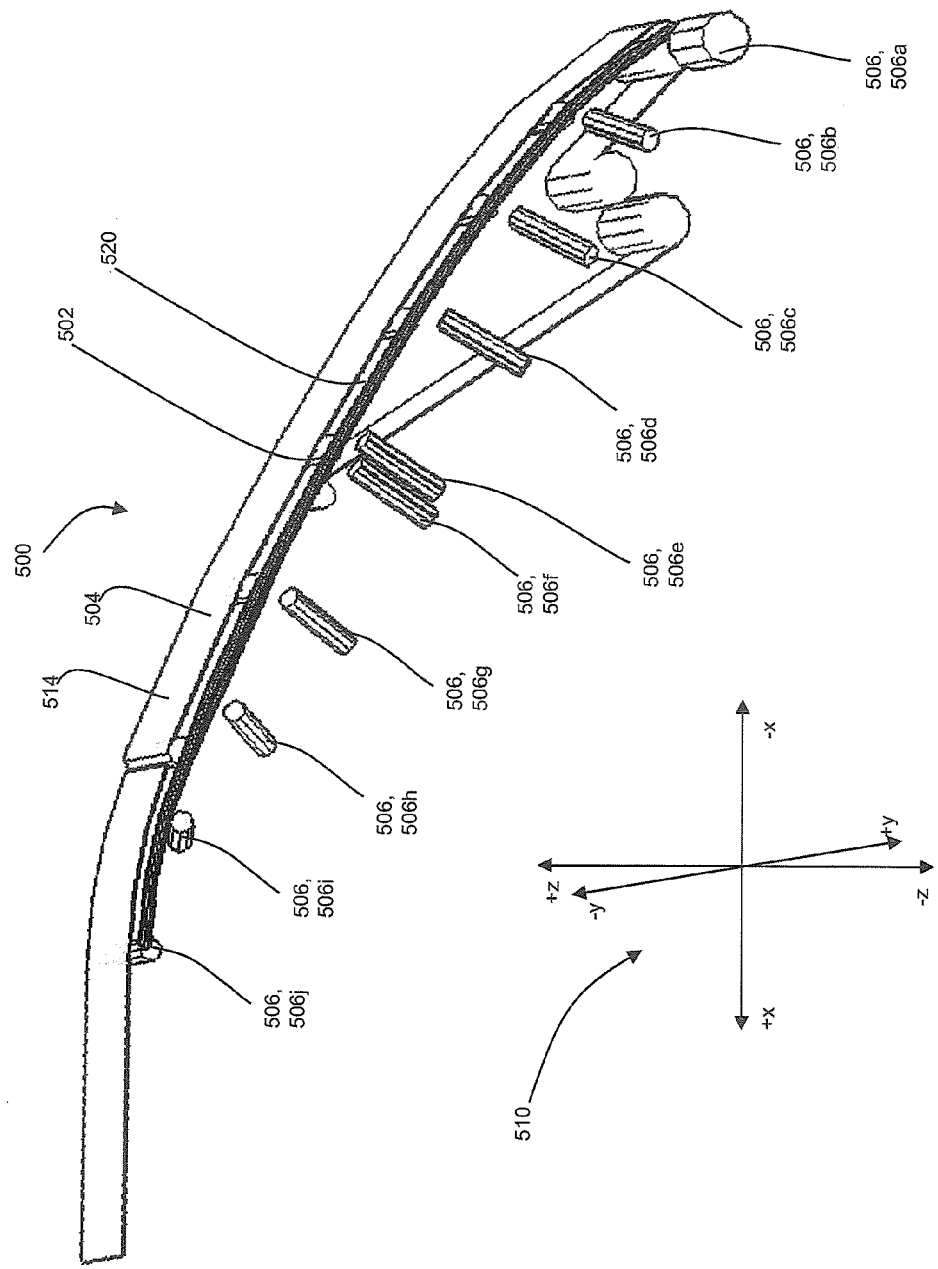
FIG. 8 is an isometric side view of the folding apparatus of FIG. 6.
Figure 9:
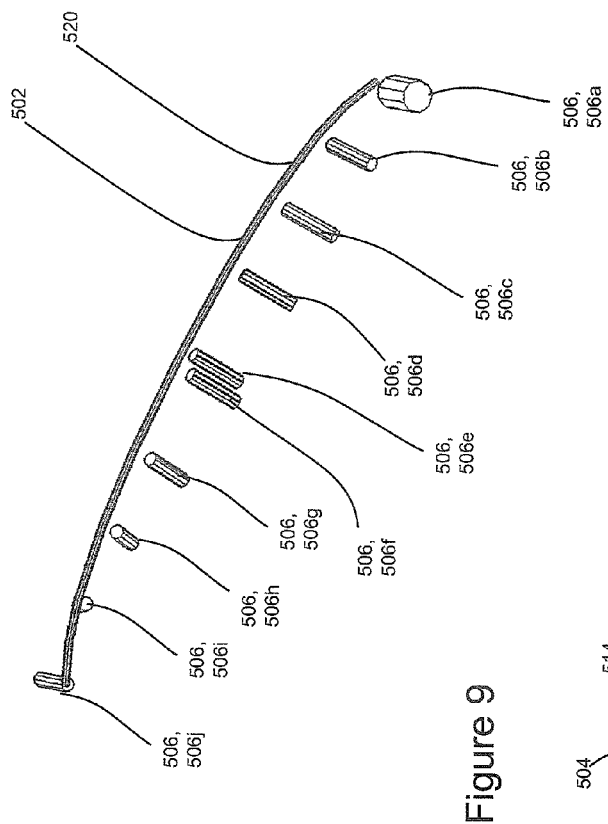
FIG. 9 is an isometric side view of a plurality of rollers and folding axis of FIG. 8.
Figure 10:
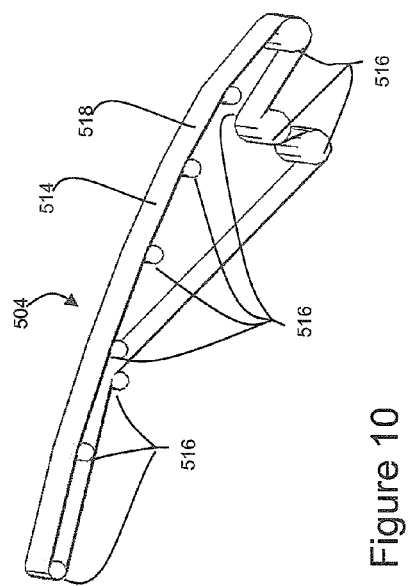
FIG. 10 is an isometric side view of a conveyor of FIG. 8.
Figure 11:
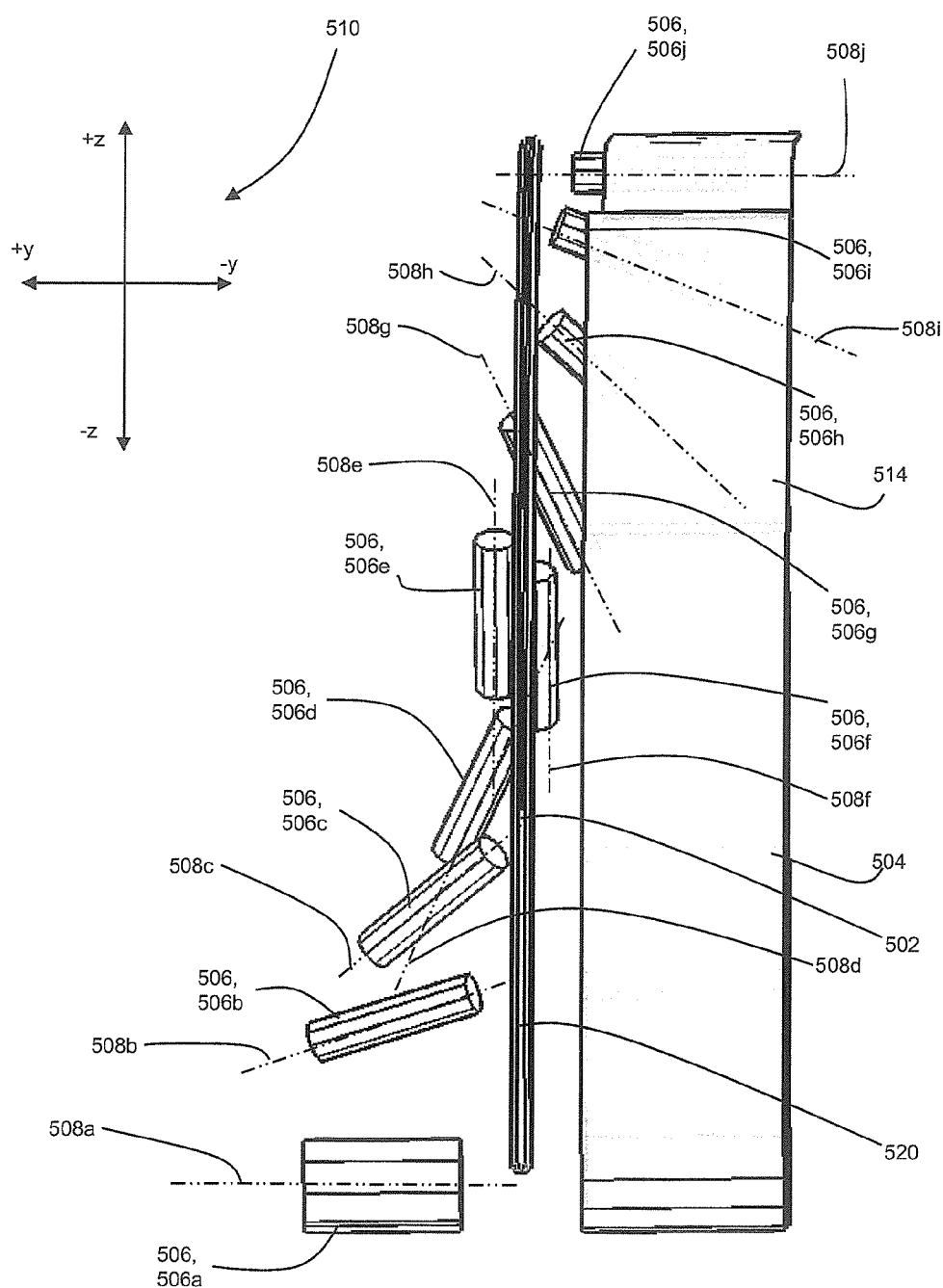
FIG. 11 is an end view of the folding apparatus of FIG. 8 looking downstream in the machine direction.
Figure 11A:
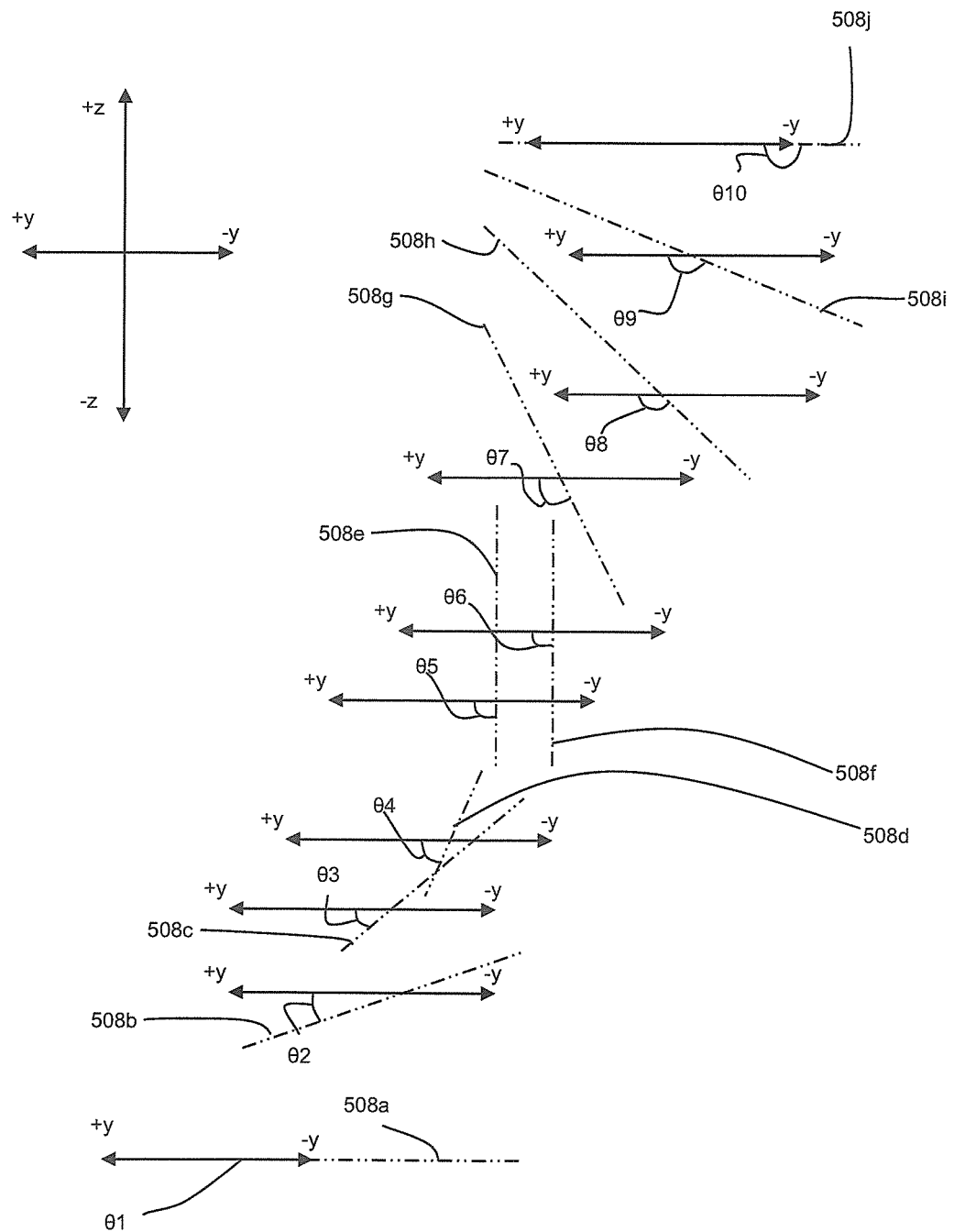
FIG. 11a illustrates the angles between the axes of rotation of the plurality of rollers and the +y axis of the folding apparatus of FIG. 11.

Upon engaging the folding apparatus 500, the conveyor 504 advances the first belt material substrate 406 and first waist regions 116 of the chassis 102 in the machine direction MD along the first web path. As shown in FIGS. 6, 8, and 10, the conveyor defines a curved path having +z and +x directional components along the MD direction. It is to be appreciated that various type of conveyor arrangements may be used. For example, as shown in FIG. 10, the conveyor 504 may include an endless belt 514 supported by a plurality of rollers 516. The endless belt 514 may define a carrier surface 518 that contacts the wearer facing surface 312 of the first belt substrate 406 and/or the inner, body facing surface 132 of the first waist region 116 of the chassis 102.

As the first belt material substrate 406 and first waist regions 116 of the chassis 102 advance along the conveyor 504, the second belt material substrate 408 and second waist regions 118 of the chassis 102 advance along the second web path defined by the rollers 506. In particular, the second path defined by the rollers 506 guides and/or advances the second belt material substrate 408 and second waist regions 118 of the chassis 102 to fold the chassis 102 along the folding axis 502. At the same time, the rollers 506 advance the second belt material substrate 408 and second waist regions 118 of the chassis 102 in the machine direction and into a facing relationship with the first belt material substrate 406 and first waist regions 116 of the chassis 102. As discussed in more detail below, the folding axis 502 may be located in a cross directional position between the conveyor 504 and the rollers 506 in the upstream machine direction MD region of the folding apparatus. In addition, the folding axis 502 may be curved along the machine direction. For example, the folding axis 502 shown in FIGS. 6, 8, 9, and 11 defines a curved path having +z and +x directional components along the MD direction.

As previous mentioned, the folding apparatus may include a plurality of rollers 506 that define the second web path. For example, the folding apparatus 500 of FIGS. 6, 8, 9, and 11, includes ten rollers 506a-506j spaced from each other along the machine direction MD. Five rollers 506a-506e in the upstream machine direction MD of the folding apparatus 500 contact the wearer facing surface 312 of the second belt substrate 408, and five rollers 506f-506j in the downstream machine direction MD of the folding apparatus 500 contact the garment facing surface 314 of the second belt substrate 408. Each roller 506a-506j also defines a rotation axis 508a-508j, respectively.

As mentioned above, the rotation axis 508a-508j of each roller 506a-506j may be angularly offset relative to the rotation axis of a preceding roller upstream in the machine direction MD. One example configuration of the aforementioned angular offset may described with reference to FIGS. 6, 8, 11, and 11a and the illustrated x-y-z coordinates 510, and in particular, may be described based on angles defined between each rotation axis 508a-508j and the +y axis. As shown, the first rotation axis 508a is aligned with the +y axis, and as such, a first angle, $\theta1$, defined between the rotation axis 508a of the first roller 506a the +y axis is 0°. The second rotation axis 508b of the second roller 506b is angularly offset from the first rotation axis 508a, and as such, a second angle, $\theta2$, defined between the second rotation axis 508b and the +y axis is greater than the first angle, $\theta1$. The third rotation axis 508c of the third roller 506c is angularly offset from the second rotation axis 508b, and as such, a third angle, $\theta3$, defined between the third rotation axis 508c and the +y axis is greater than the second angle, $\theta2$. The fourth rotation axis 508d of the fourth roller 506d is angularly offset from the third rotation axis 508c, and as such, a fourth angle, $\theta4$, defined between the fourth rotation axis 508d and the +y axis is greater than the third angle, $\theta3$. The fifth rotation axis 508e of the fifth roller 506e is angularly offset from the fourth rotation axis 508d, and as such, a fifth angle, $\theta5$, defined between the fifth rotation axis 508e and the +y axis is greater than the fourth angle, $\theta4$.

In the arrangement shown in FIGS. 6, 8, 11, and 11a, the sixth rotation axis 508f of the sixth roller 506f is not angularly offset from the fifth rotation axis 508e, and as such, a sixth angle, $\theta6$, defined between the sixth rotation axis 508f and the +y axis is the same as the fifth angle, $\theta5$. The seventh rotation axis 508g of the seventh roller 506g is angularly offset from the sixth rotation axis 508f, and as such, a seventh angle, $\theta7$, defined between the seventh rotation axis 508g and the +y axis is greater than the sixth angle, $\theta6$. The eighth rotation axis 508h of the eighth roller 506h is angularly offset from the seventh rotation axis 508g, and as such, an eighth angle, θ8, defined between the eighth rotation axis 508h and the +y axis is greater than the seventh angle, θ7. The ninth rotation axis 508i of the ninth roller 506i is angularly offset from the eighth rotation axis 508h, and as such, a ninth angle, θ9, defined between the ninth rotation axis 508i and the +y axis is greater than the eighth angle, θ8. The tenth rotation axis 508j of the tenth roller 506j is angularly offset from the ninth rotation axis 508i, and as such, a tenth angle, θ10, defined between the tenth rotation axis 508j and the +y axis is greater than the ninth angle, θ9.

It is to be appreciated that various embodiments of the folding apparatus 500 may include various quantities of rollers 506 angularly offset from each other in various ways. For example, Table 1 below shows one embodiment of an angular offset arrangement of the rollers 506 shown in FIGS. 6, 11, and 11a.

TABLE 1

| Roller | Rotation Axis | Angle Between Rotation Axis and +y Axis | Relative Angular Offset with Respect to Upstream Rotation Axis |
|---|---|---|---|
| 506a | 508a | θ1 = 0° | |
| 506b | 508b | θ2 = 22.5° | 22.5° |
| 506c | 508c | θ3 = 45° | 22.5° |
| 506d | 508d | θ4 = 67.5° | 22.5° |
| 506e | 508e | θ5 = 90° | 22.5° |
| 506f | 508f | θ6 = 90° | 0° |
| 506g | 508g | θ7 = 112.5° | 22.5° |
| 506h | 508h | θ8 = 135° | 22.5° |
| 506i | 508i | θ9 = 157.5° | 22.5° |
| 506j | 508j | θ10 = 180° | 22.5° |

As shown in the FIGS. 6, 8, 9, and 11, the folding axis 502 may be defined by a rail 520 around which the crotch region 120 of the advancing chassis 102 may be folded. As previously mentioned, the folding axis 302 extends in the machine direction and may be curved. For example, the curved folding axis 502 shown in FIGS. 6, 8, 9, and 11 defines has both +z and +x directional components along the MD direction. It is to be appreciated that the folding axis 502 may be defined in various ways and may extend in various lengths along the machine direction MD. In some embodiments, the folding axis 502 may be defined by a continuous arc. In other embodiments, the folding axis 502 may be defined by a plurality of arcs of different radii. In yet other embodiments, the folding axis 502 may be defined by one or more arcs in combination with one or more straight portions. In some embodiments, the folding axis 502 may include straight segments connected arcuate segments. In some embodiments, such straight segments may approximate a chord of the ideal folding rail arc between successive folding segments. It is also to be appreciated that in some embodiments, the folding axis 502 may be defined by an edge of conveyor 504.

Figure 12:
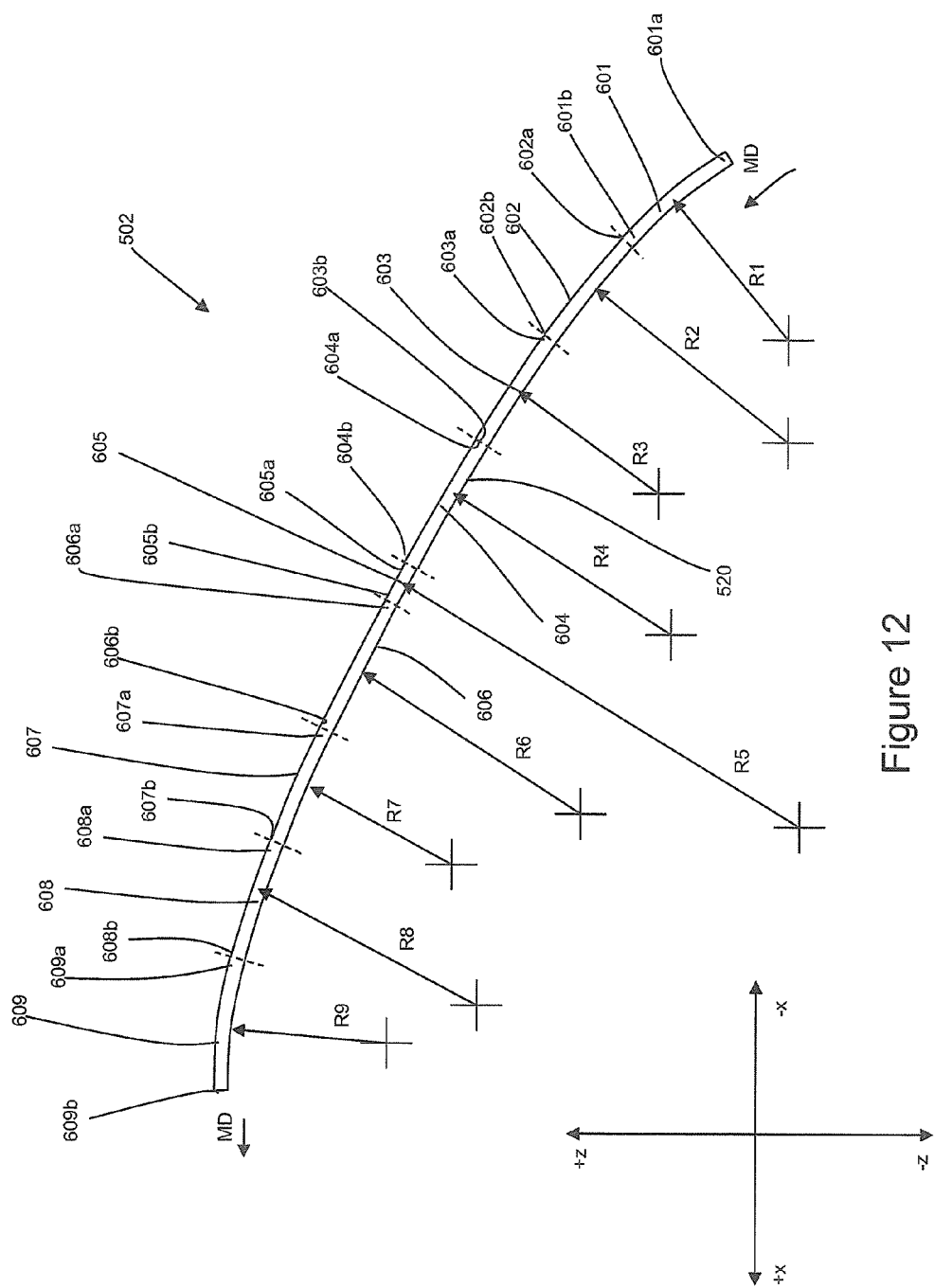
FIG. 12 is a side view of an embodiment of a folding axis.

FIG. 12 shows an example of a folding axis 502, which may also be defined by a rail 520. The folding axis 502 in FIG. 12 is defined by nine segments 601-609. More particularly, the folding axis 502 extends in the machine direction MD from a first segment 601 to a ninth segment 609 along a curved path having +x and +z components. More particularly, the folding axis 502 extends in the machine direction MD from a first segment 601 extending between a first end portion 601a and a second end portion 601b; to a second segment 602 extending between a first end portion 602a and a second end portion 602b; to a third segment 603 extending between a first end portion 603a and a second end portion 603b; to a fourth segment 604 extending between a first end portion 604a and a second end portion 604b; to a fifth segment 605 extending between a first end portion 605a and a second end portion 605b; to a sixth segment 606 extending between a first end portion 606a and a second end portion 606b; to a seventh segment 607 extending between a first end portion 607a and a second end portion 607b; to an eighth segment 608 extending between a first end portion 608a and a second end portion 608b; and to a ninth segment 609 extending between a first end portion 609a and a second end portion 609b.

It is to be appreciated that some segments 601-609 of the folding axis 502 may have the same or different lengths; may be straight; and may be curved, wherein such curves may be defined by the same or different radii R1-R9. For example, Table 2 below shows the relative lengths as defined by various radii extending along various arc angles.

TABLE 2

| Segment | Radius | Arc Angle |
|---|---|---|
| 601 | R1 = 1.1 meters | 17° |
| 602 | R2 = 2.9 meters | 6° |
| 603 | R3 = 4.3 meters | 4° |
| 604 | R4 = 6.7 meters | 3° |
| 605 | R5 = see note below | See note below |
| 606 | R6 = 6.7 meters | 3° |
| 607 | R7 = 4.3 meters | 4° |
| 608 | R8 = 2.9 meters | 6° |
| 609 | R9 = 1.1 meters | 17° |

Note:
In the embodiment of Table 2, the fifth segment 605 is a straight 25 mm length.

Figure 13:
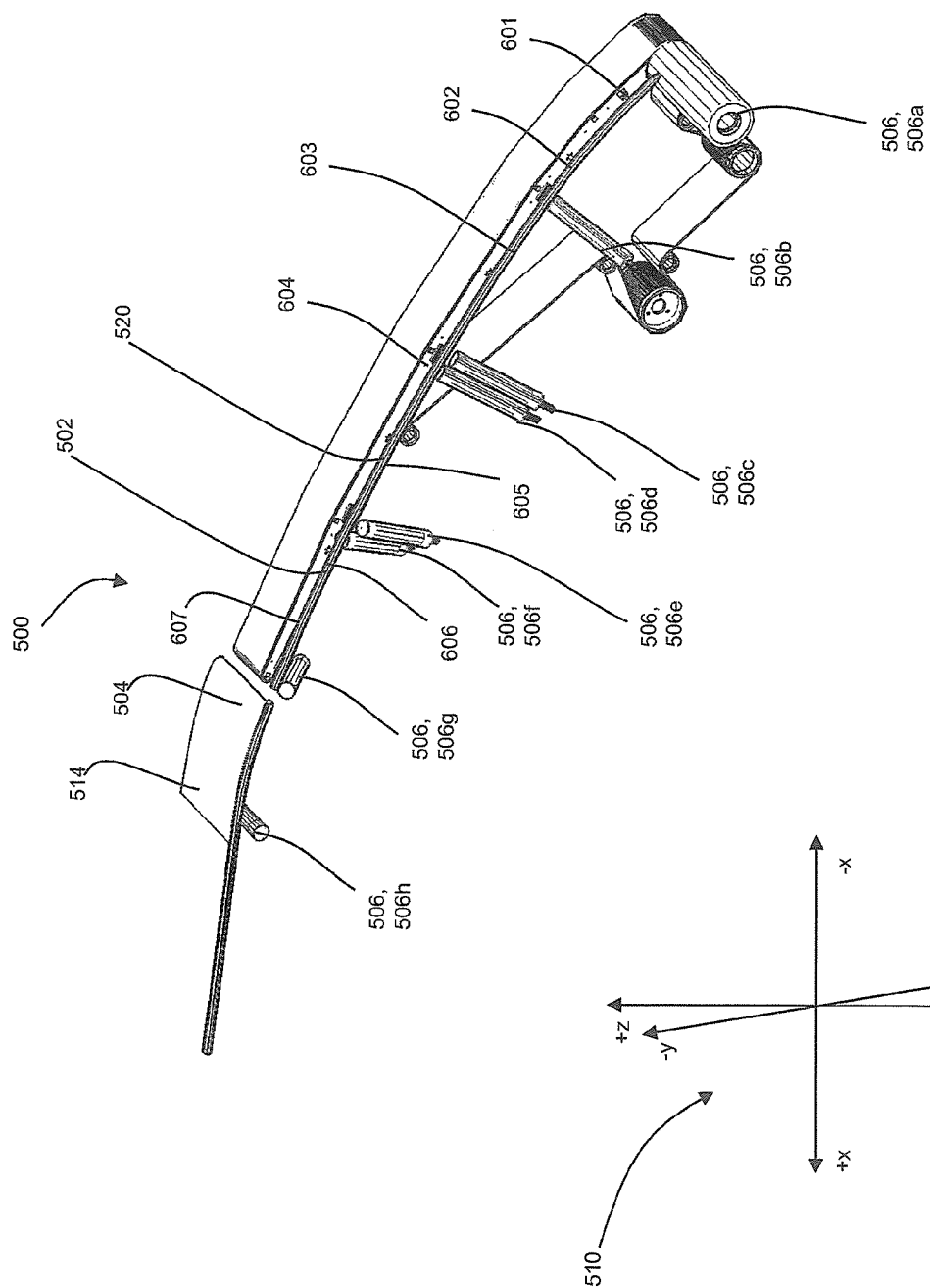
FIG. 13 is an isometric side view of a second embodiment of a folding apparatus.

As previously mentioned, it is to be appreciated that various embodiments of the folding apparatus 500 may include various quantities of rollers 506 angularly offset from each other in various ways. For example, FIG. 13 shows another embodiment of a folding apparatus including eight rollers 506. Consistent with the description provided above with reference to Table 1 and associated FIGS. 11, 11a, and 12, Table 3 below shows one embodiment of an angular offset arrangement of the rollers 506 shown in FIG. 13.

TABLE 3

| Roller | Rotation Axis | Angle Between Rotation Axis and +y Axis | Relative Angular Offset with Respect to Upstream Rotation Axis |
|---|---|---|---|
| 506a | 508a | θ1 = 0° | |
| 506b | 508b | θ2 = 36° | 36° |
| 506c | 508c | θ3 = 70° | 34° |
| 506d | 508d | θ4 = 74° | 4° |
| 506e | 508e | θ5 = 105° | 32° |
| 506f | 508f | θ6 = 110° | 4° |
| 506g | 508g | θ7 = 144° | 34° |
| 506h | 508h | θ8 = 180° | 36° |

FIG. 13 also shows an example of a folding axis 502, which may also be defined by a rail 520 similarly described above with reference to FIGS. 11, 11a, and 12. As shown in FIG. 13, the folding axis 502 may be defined by seven segments 601-607, and Table 4 below shows examples of relative lengths of the segments as defined by various radii extending along various arc angles.

TABLE 4

| Segment | Radius | Arc Angle |
|---|---|---|
| 601 | R1 = 1.9 meters | 17.5° |
| 602 | R2 = 5.6 meters | 5.9° |

TABLE 4-continued

| Segment | Radius | Arc Angle |
|---|---|---|
| 603 | R3 = 8.0 meters | 0.5° |
| 604 | R4 = 7.5 meters | 4.2° |
| 605 | R5 = 8.0 meters | 0.5° |
| 606 | R6 = 5.0 meters | 6.0° |
| 607 | R7 = 1.9 meters | 15.4° |

As discussed above with regard to the folding processes herein, the first end region of the advancing substrate travels in the machine direction along a first web path during the folding process while the second end region of the substrate travels in the machine direction along a second web path defining a helical shape. The folding axis may also be defined by an arc extending in the machine direction MD, wherein the second end region of the advancing substrate is helically folded toward the inside of the arc. Further, the folding apparatus including a curved or arc-shaped folding axis may be configured such the first and second web paths have substantially equal lengths.

In some embodiments, the length of the first web path may be defined by the travel path of substrate 406 as the substrate 406 advances along the conveyor 504 from the first end position 601a to the second end position 609b of the folding axis 502. And the length of the second web path may be defined by the travel path of the substrate 408 as the substrate 408 advances in the machine direction along rollers 506a through 506j. For each segment between consecutive rollers 506, the length of the second web path may be calculated by solving for a three-dimensional distance between contact points of substrate 408 against the rollers 506 given an assumed arc distance along the curved folding axis 502 and an assumed relative angular offset between consecutive rollers 506a through 506j. The distance between contact points of substrate 408 at the edge closest to folding axis 502 may be solved to be equal to the distance between the contact points of substrate 408 at the edge farthest from folding axis 502 by varying the angle between the rotation axis and the +y-axis, as shown in Table 2 above.

It is to be appreciated that the apparatuses and methods herein may be configured to provide for relatively low web strains and maintain relatively flat webs during the folding process. In some embodiments, the web strain of the outboard edge of the second web path may therefore the same as the web strain of a continuous web along the folding axis 502. In some embodiments, the rollers may be slightly displaced from the initial positions to help improve traction of substrate 408 on the rollers 506, and to help maintain substrate 408 substantially in contact with each roller along the cross machine direction. The helical path substantially defines the contact points of the substrate 408, and the rollers may be displaced on either surface of substrate 408. With a known distance between consecutive rollers 506, known rotation angle of each roller 506, the second web path may be fully defined. In such an initial condition, the web strain in web path 408 may substantially match the design strain at folding axis 502. In some embodiments, the design strain may be within a range of 0.5% to 2.0% machine direction (MD) strain, and may be 1.25% MD strain. Such a condition may exist for the inboard and outboard portions of the second substrate 408. In the center of substrate 408, the web strain may be as low as 0.1%. In some instances, a slight offset of the rotational angle may be sufficient to balance the MD strain of the inboard edge of substrate 408 and the outboard edge of substrate 408. In some embodiments, values for the MD strain at the inboard edge of substrate 408 may be 0.1% to 0.3%. In other embodiments, values for the MD strain at the inboard edge of substrate 408 may be 0.5%, and in some instances, as high as 1.25% to match the MD strain at the folding axis 502. In some embodiments, the MD strain at the center of substrate 408 may be about 0.2%.

It is to be appreciated that various embodiments of methods and apparatus may include varying fold angles between adjacent rollers, angles of folding axis between adjacent rollers, and span lengths between adjacent rollers. It is also to be appreciated that the pattern of idlers in the folding apparatus may vary substantially. Solutions of idler angle of rotation in a plane normal to the folding axis and curvature of the helical path may exist for any span length. Embodiments with small angular rotation of the fold between spans and short spans may be possible, as embodiments with large rotations of the folding web around the fold axis, with corresponding larger span lengths. Straight segments with nominally no folding may be added at any point in the fold, and may be added at the midpoint of the fold, to allow consecutive rollers to contact alternate sides of the web.

In some embodiments, the apparatus may be configured to exert and/or maintain cross direction tension on the substrate. For example, in some embodiments, folding apparatus may be configured such that the outboard edge of the substrate has a longer path length than the opposing outboard edge. In some configurations, the path length may be 0.5 to 2% longer. In yet another example, the apparatus may be configured with tapered rollers having relatively larger diameters near the outboard edge of the substrate and relatively smaller diameters near the fold line of the substrate. In yet other configurations, the apparatus may include skewed rollers, such that the axis of revolution of each roller is not in a plane normal to the fold axis. It is also to be appreciated that other devices may be used to provide a web spreading function, including for example, static bars, folding plows, curved static bars such as bow or banana bars, elastomeric idlers including those with deformable spreading surfaces such as an Arco roller from American Roller, Inc., Mt. Hope rolls, and many other devices. Such spreading devices may comprise the folding rollers or may be additional to the folding rollers.

In some embodiments, the folding apparatus may include an arrangement for anchoring the non-folded side of the substrate. More particularly, an anchoring mechanism may be used such that the folding side of the web can be pulled in a cross directional direction via an arrangement of components touching the web, such as rollers, folding plows, driven rollers or the like, while the non-folded side is transported without folding and with little or no change of position in the cross-machine direction. In some embodiments, the anchoring mechanism may include a vacuum conveyor, which may also include a pitched belt such that vacuum holes are primarily under impermeable film sections of the substrate being folded. In yet other embodiments, the anchoring mechanism may operate to compress of the substrate between opposing belts or rollers. In some embodiments, the compression or vacuum used to control the substrate may occur primarily at the crotch region. In some embodiments, spring loaded rollers, pneumatically engaged rollers, pneumatic tires, internally pressurized elastomeric elements, elastomeric rollers, elastomeric rollers with internal voids may be used to control the pad.

In some embodiments of the folding apparatus, the line of contact of the substrate at each folding roller may be tangent to the outboard surface of the folding rail. The solution of sequential cross-sections of the web as it revolves around the folding axis describes the position of the article which is being folded. The rollers which contact the article may be on either the inside or outside of the web. It may also be possible to displace idlers from the ideal tangent solution to increase wrap angle on roller elements. In some embodiments, rollers are displaced from the ideal tangent contact, equal strain solution to ensure the web has a non-zero contact length with each roller element. Displacement of idlers may be in the Y or Z direction. In some embodiments, rollers at closely spaced pairs with alternating contact sides may be displaced to ensure full width contact. In some embodiments, the last, horizontal, roller is displaced to avoid interference with a folding rail or conveyor.

In some embodiments, the folding apparatus is followed by a waist alignment unit, that may include upper and/or lower vacuum conveyors. Such conveyors may pivot to provide a web steering function to align features of the folded and non-folded sides of the article, either relative to each other or relative to a reference value. Detection of the tracking position may be by dedicated sensor or a machine vision system. In some embodiments, edges of a waist belt on the folded side and the non-folded side of an article are detected using an FR6001 sensor commercially available from Erhardt+Leimer. In some embodiments, these sensors are mounted on a singled fixed bracket, and setpoint adjustments are made by changing a variable in the electronic controller. In some embodiments, the waist alignment unit may be replaced by a tracking device at one of the folding board rollers, which may include a camber roller replacing one or more of the folding rollers 506a-j. Such a camber roller may also be feedback controlled via a downstream sensor or vision system.

To maintain machine direction alignment of the folding and non-folding portions of the substrate, one of more elements of the drive system may have a controllable velocity. In some embodiment, the speed of a downstream drive point, preferably a vacuum conveyor may be varied, while maintaining the folding conveyor and a downstream drive point for the non-folded side at a constant surface velocity. Such velocity control may be open loop, but may also be accomplished by closed loop feedback control based upon signals from downstream sensors or machine vision systems. An example of such a feedback control system is a Proportional-Integral-Derivative (PID) controller, optionally with feed-forward and speed compensation, such as is implemented in common industrial controllers, such as the ControLogix platform from Rockwell Automation. The input signal may also include a position offset between folded and unfolded features on one or a series of articles. The input signal may also be a time difference measured between features on folded and unfolded portions of one or a series of articles. It is also to be appreciated that the machine direction alignment of features on folded and unfolded portions of one or a series of articles may also be accomplished by varying the path length of either the folded or unfolded portion of the substrate.

In some embodiments, the substrate may be delivered flat at the infeed of the folding system. In some embodiments, opposed pivoting camber rollers track and spread the web prior to folding. In some embodiments, the tracking function and spreading functions are feed-back controlled, using commercially available web guides. In some embodiments, the sensors of these web guides may be connected to a quality monitoring system, the edge positions of each side of the web may be stored, and/or the setpoints and control parameters may be remotely adjusted through an electronic controller. The folding centerline may be set by the cross-machine direction position of the substrate as the substrate enters the folder.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method of folding a continuous length of absorbent articles comprising a plurality of intermittently spaced chassis advancing in a machine direction, each chassis having a first end portion and an opposing second end portion separated from each other in a cross direction by a central portion, and each chassis having a first surface and an opposing second surface, the method comprising the steps of:
    providing a rail comprising curved segments;
    advancing the first end portions of the chassis in the machine direction on a first web path;
    advancing the second end portions of the chassis in the machine direction on a second web path to fold the second end portions of the chassis 180° around the curved segments of the rail to position the second surfaces of the second end portions of the chassis into a facing relationship with the second surfaces of the first end portions of the chassis as the chassis advance in machine direction; and
    advancing the central portions of the chassis in the machine direction on the curved segments of the rail while folding the second end portions, wherein the central portion of each chassis is advanced along the curved segments of the rail simultaneously as the second end portion of the chassis is folded 180° around the curved segments of the rail to position the second surface of the second end portion of the chassis into a facing relationship with the second surface of the first end portion of the chassis, wherein a plurality of the curved segments of the rail are defined by different radii such that the second web path and the first web path comprise substantially equal lengths.

2. The method of claim 1, wherein the rail comprises nine curved segments having five different lengths.

3. The method of claim 1, wherein the rail further comprises a straight segment positioned between two curved segments.

4. The method of claim 1, wherein the rail comprises seven curved segments having five different lengths.

* * * * *